United States Patent
Faulstich et al.

(10) Patent No.: US 12,281,295 B2
(45) Date of Patent: Apr. 22, 2025

(54) HARVESTING DEVICE AND METHOD FOR HARVESTING THE CONTENT OF A BIOREACTOR BAG

(71) Applicant: Sartorius Stedim Switzerland AG, Tagelswangen (CH)

(72) Inventors: Franziska Faulstich, Göttingen (DE); Fabian Tunzini, Winterthur (CH); Thorsten Adams, Göttingen (DE)

(73) Assignee: Sartorius Stedim Switzerland AG, Tagelswangen (CH)

( * ) Notice: Subject to any disclaimer, the term of this patent is extended or adjusted under 35 U.S.C. 154(b) by 1021 days.

(21) Appl. No.: 17/269,438

(22) PCT Filed: Aug. 27, 2019

(86) PCT No.: PCT/EP2019/072736
§ 371 (c)(1),
(2) Date: Feb. 18, 2021

(87) PCT Pub. No.: WO2020/048812
PCT Pub. Date: Mar. 12, 2020

(65) Prior Publication Data
US 2021/0324320 A1    Oct. 21, 2021

(51) Int. Cl.
*C12M 1/26* (2006.01)
*C12M 1/00* (2006.01)
(Continued)

(52) U.S. Cl.
CPC ............ *C12M 33/00* (2013.01); *C12M 23/14* (2013.01); *C12M 23/46* (2013.01); *C12M 23/48* (2013.01); *F16M 11/2021* (2013.01)

(58) Field of Classification Search
CPC ...... C12M 33/00; C12M 23/48; C12M 23/14; C12M 23/46; F16M 11/2021; E04G 5/00
See application file for complete search history.

(56) References Cited

FOREIGN PATENT DOCUMENTS

DE    4405977 A1 * 9/1995 ............... E04G 5/00
EP    2740787 A1 * 6/2014 ............ C12M 21/02
(Continued)

OTHER PUBLICATIONS

International Search Report issued in International Application No. PCT/EP2019/072736 issued on Nov. 8, 2019.

*Primary Examiner* — Michael L Hobbs
(74) *Attorney, Agent, or Firm* — Quinn IP Law

(57) ABSTRACT

The invention relates to a harvesting device (100, 100a, 100b, 100c, 100d) for harvesting a content of a bioreactor bag (102) and to a method for harvesting a content of a bioreactor bag (102). The harvesting device (100, 100a, 100b, 100c, 100d) comprises: a first fixing device (104) for fixing one of the fixing portions (112, 114) to the harvesting device (100, 100a, 100b, 100c, 100d), a second fixing device (106) for fixing the other of the fixing portions (112, 114) to the harvesting device (100, 100a, 100b, 100c, 100d), a base (108), and an adjusting device (110) coupling the first fixing device (104) and/or the second fixing device (106) to the base (108). The adjusting device (110) is configured to selectively allow changing an arrangement of the first fixing portion (112) and/or the second fixing portion (114) relative to the base (108) or fixing the arrangement of the first fixing portion (112) and/or the second fixing portion (114) relative to the base (108).

14 Claims, 11 Drawing Sheets

Figure 1:
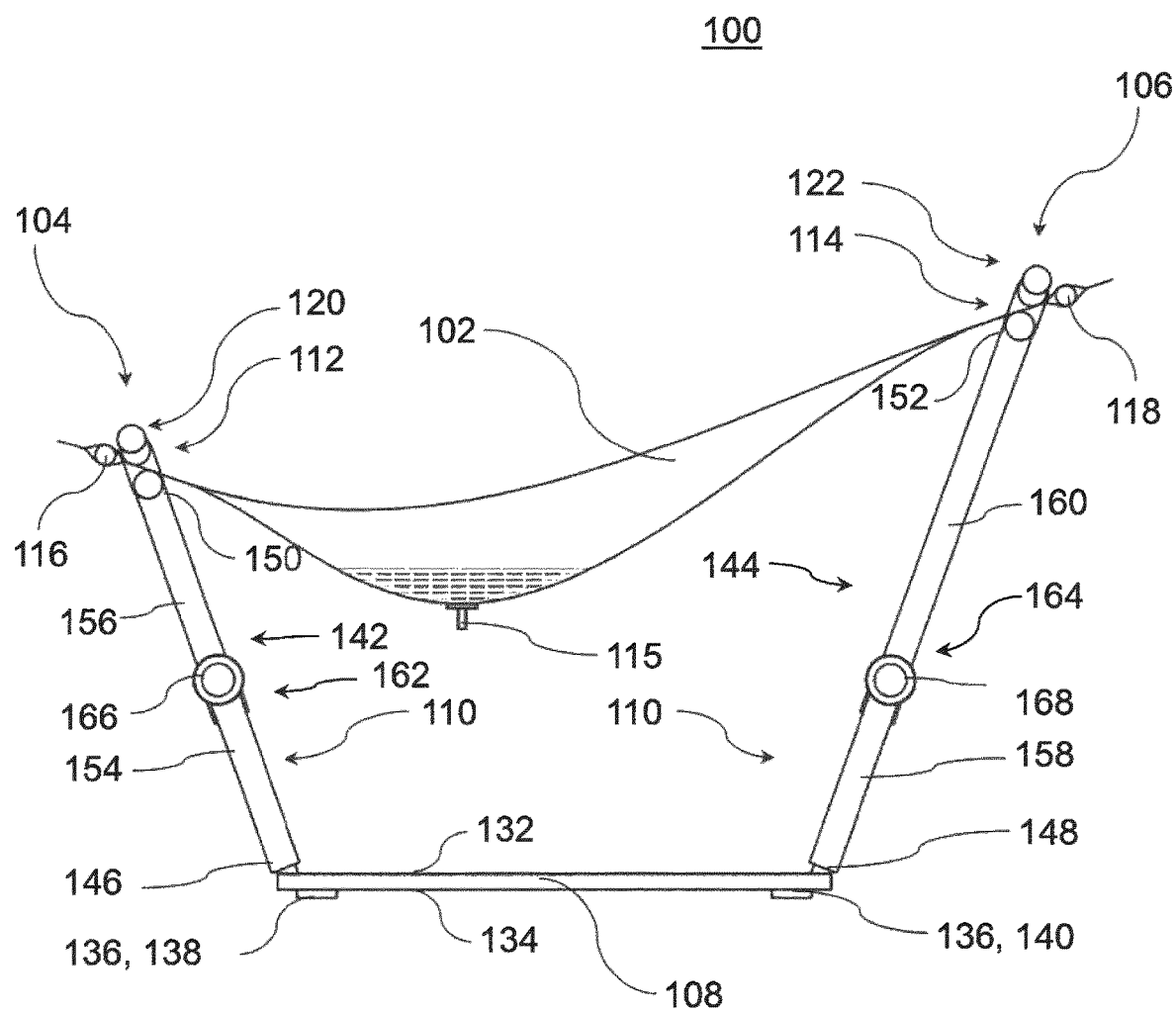

(51) Int. Cl.
*C12M 3/00* (2006.01)
*F16M 11/20* (2006.01)

(56) References Cited

FOREIGN PATENT DOCUMENTS

| | | | |
|---|---|---|---|
| WO | 2010096545 A2 | 8/2010 | |
| WO | WO-2012115581 A1 * | 8/2012 | ............ C12M 21/02 |
| WO | 2012129681 A1 | 10/2012 | |

* cited by examiner

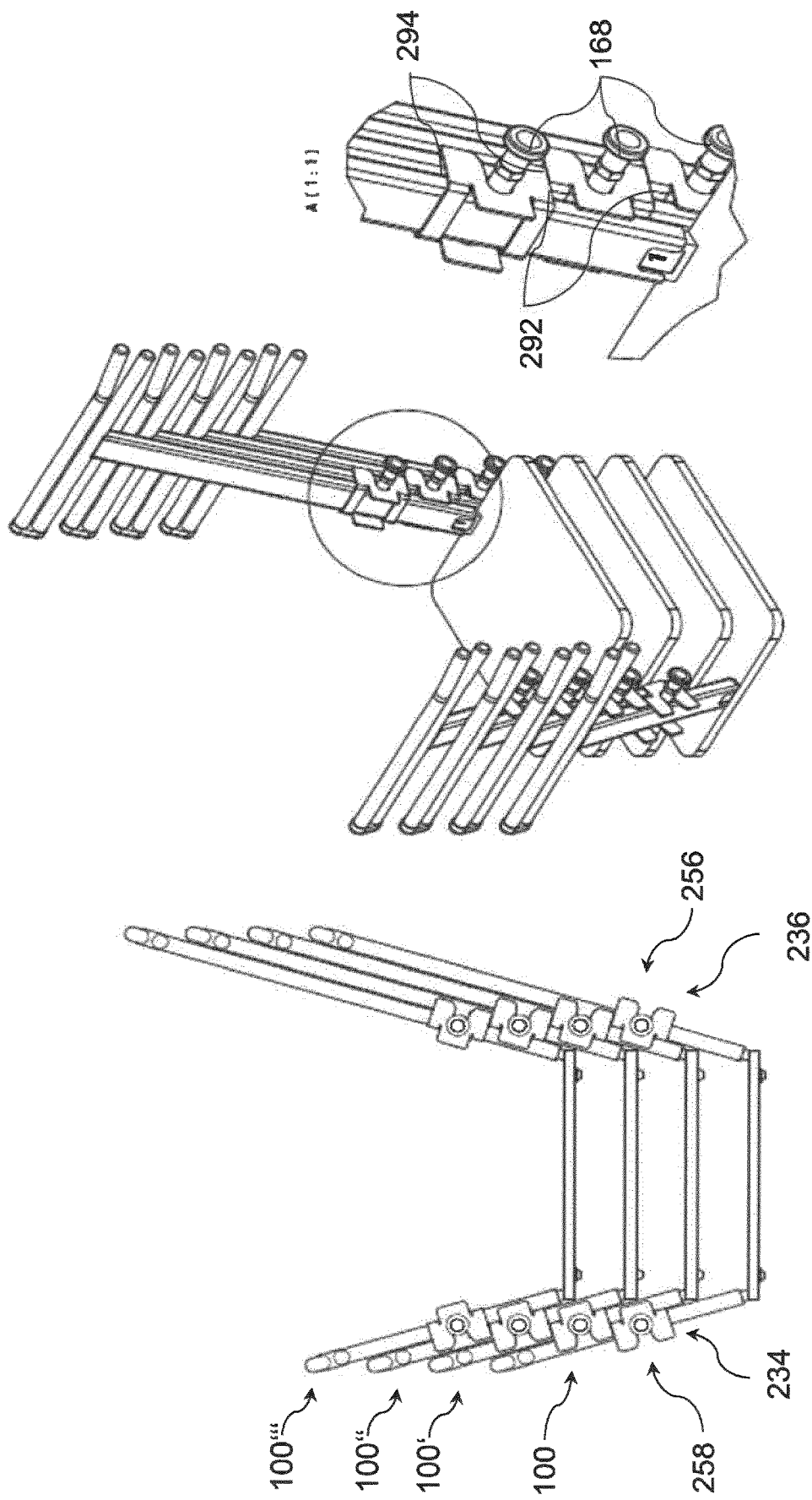

HARVESTING DEVICE AND METHOD FOR HARVESTING THE CONTENT OF A BIOREACTOR BAG

The present invention relates to a harvesting device for harvesting a content of a bioreactor bag. The present invention further relates to a method for harvesting a content of a bioreactor bag.

In many industrial sectors, bioreactor bags are used for mixing or circulating substances. In the production of culture media for microorganisms or in controlled biotechnological processes such as cell cultivation, the mixing or circulation of the container content is of particular importance.

The use of flexible disposable bioreactor bags from films increases in importance in particular with regard to the constantly increasing requirements for the sterility of the processes in bioprocess engineering with respect to rigid containers made of glass or stainless steel. In addition to good sterilizability, the film bags offer further advantages such as cost-effective production, the simple and space-saving storage, the greatest possible safety against contamination and the omission of a complex cleaning after use.

Bioreactors in the classical biopharma usually comprise a moving and/or tempering device. After sufficient tempering and mixing of the content of the flexible disposable bioreactor bags, the content of the bioreactor bag has to be harvested.

EP 2 975 111 B1 describes a mixing device for mixing the content of a container comprising a container support for supporting the container and a moving device connected to the container support in order to be able to mix the content of the container in a mixing position. The container support is supported pivotally about a removal axis relative to the moving device in order to be able to displace the container into a removal position for removing and harvesting the content of the container. The mixing device described in EP 2 975 111 B1, thus, enables both the mixing and harvesting of the content of the container. For harvesting of the content of the container, the container has to be displaced around a removal pivot axis into a particular removal position, in which the cultivated cells are gathered in the vicinity of a harvesting port, which is arranged at one of the bottom corners of the bag, by use of gravity.

In classical biopharma, where cell cultures are applied to produce a (therapeutic) molecule, harvesting or transfer from the bioreactor bag to the subsequent bag or vessel is mostly done by pumping out the cell suspension. In contrast, cell harvesting in cell therapy settings is mostly done by gravity as these cells are very sensitive to shear stress that would be applied by pumping. After the end of the cultivation, the bioreactor bag may be taken off the bioreactor tray and an operator usually holds the bioreactor bag above the level of the target bag which is placed on a table or lab bench, for example. Due to the current bag port design in standard bags, it is difficult to gather the cultivated cells in the vicinity of the harvesting port and/or to completely remove the liquid from the bag. The operator aims to remove as much liquid (and thereby therapeutic cells) as possible by squeezing and re-positioning the bag manually. The problem for draining rocking motion bags completely is not properly addressed as these bioreactor bags usually do not have ports at edges or welded into the side. This leads to the practice of an operator standing there for around 10 minutes or more until the bag is completely empty, or at least the remaining trapped volume cannot be removed anymore.

It is the object of the present invention to provide a harvesting device and a method for harvesting a content of a bioreactor bag which enables to improve productivity of bioreactor processes.

This object is achieved by the subject matter of the independent claims. Preferred embodiments can be derived from the dependent claims.

According to the present invention, a harvesting device for harvesting a content of a bioreactor bag is provided, wherein the bioreactor bag has fixing portions at both longitudinal ends thereof and a harvesting port for draining the content of the bioreactor bag provided between said longitudinal ends, wherein the harvesting device comprises: a first fixing device for fixing one of the fixing portions to the harvesting device, a second fixing device for fixing the other of the fixing portions to the harvesting device, a base, and an adjusting device coupling the first fixing device and/or the second fixing device to the base. The adjusting device is configured to selectively allow changing an arrangement of the first fixing portion and/or the second fixing portion relative to the base or fixing the arrangement of the first fixing portion and/or the second fixing portion relative to the base, and the harvesting device is configured such that the bioreactor bag can be arranged and fixed in a harvesting arrangement in which the bioreactor bag hangs between the first fixing device and the second fixing device with the harvesting port being positioned substantially at the lowermost point of the bioreactor bag.

Advantageously, the harvesting device allows harvesting of the cells cultivated in the bioreactor bag independently from the bioreactor device, the bioreactor device including a moving device and/or a tempering device, so that the bioreactor device may be used to cultivate cells of the next bioreactor bag while the content of the first bioreactor bag is being harvested. Moreover, the possibility to adjust the arrangement of the bioreactor bag such that the harvesting port is positioned substantially at the lowermost point of the bioreactor bag, enables to optimize the harvesting process by use of gravity, regardless of the configuration and/or production tolerances of the bioreactor bag, and simplifies the harvesting process for the operator.

The present invention describes a harvesting device to be used for all kinds of flexible bag containers, including bioreactor bags, particularly disposable bioreactor bags. The bioreactor bag can be produced from a film or sheet material. Such a bioreactor bag can comprise edges welded at least on two opposite sides, e.g., on a first side and on a second side in a longitudinal axis of the bioreactor bag. The bioreactor bag can also further comprise welded edges on two opposite sides in a width direction perpendicular to the longitudinal axis. In a plan view, the bioreactor bag can have a substantially rectangular or square shape. Adjacent to the two opposite sides in the longitudinal direction, the bioreactor bag can have fixing portions, e.g., a first fixing portion adjacent to the first side of the bioreactor bag and a second fixing portion adjacent to the second side of the bioreactor bag. The fixing portions may extend across substantially the width of the bioreactor bag. Each of the fixing portions is preferably formed as a thickened portion. The thickened portion may comprise an elongated rod or tube, which may be welded into the bioreactor bag or otherwise fixed to the bioreactor bag. The first thickened portion may comprise a first rod or tube and the second thickened portion may comprise a second rod or tube. The rods or tubes may be formed of elastic material and may extend between the two opposite sides in the width direction of the bioreactor bag, preferably in an angle of about 90° with respect to the longitudinal axis of the bioreactor bag. The first and second fixing portions or the first and second rods may be parallel to each other. It is noted that the fixing portions are not limited to thickened portions and may also comprise holes, slots, adhesives, hook and loop fasteners and/or other means suitable for properly fixing the bioreactor bag to respectively configured fixing devices. The fixing devices may comprise clamps, clamping rails, fastening hooks and/or other suitable means.

The bioreactor bag can have a predetermined upper surface extending between the two opposing fixing portions. The upper surface and the lower surface opposite the upper surface refer to the two largest surfaces of the bioreactor bag. The upper surface and/or the lower surface may comprise one or more ports in addition to the harvesting port, for supplying and/or discharging liquids and/or gases to and from the inside of the bioreactor bag, and/or for introducing various types of sensors into the inside of the bioreactor bag. Preferably, the harvesting port is positioned distanced from the remaining ports of the bag. For example, the harvesting port can be arranged in the vicinity of one longitudinal end of the bag, while the other port(s) are arranged in the vicinity of the other longitudinal end and/or in a middle region of the bag. Alternatively, the lower surface can be a removal surface and can comprise the harvesting port while the other port(s) are arranged on the upper surface, wherein said removal surface may also comprise one or more additional port(s), for example sensor port(s), arranged thereon. In a configuration where a lower surface of the bioreactor bag is a removal surface and comprises the harvesting port and possibly further ports, the tray of the moving device and/or the tempering device of the bioreactor device may comprise one or more recess(es) for accommodating said port(s) during cell cultivation. Distancing the harvesting port from the other port(s) prevents liquid from entering other ports as it collects at the harvesting port where no other ports are positioned. The harvesting port can be positioned at a position in the vicinity of the longitudinal axis (centerline) of the bioreactor bag, preferably at a position on the longitudinal axis. However, the harvesting port may also be located at any position on the upper or lower surface that is offset from the longitudinal axis. The distance between the harvesting port and one of the two opposing sides of the bioreactor bag, e.g., the first side of the bioreactor bag, can be shorter than the distance between the harvesting port and the other side of the bioreactor bag, e.g., the second side of the bioreactor bag. However, the harvesting port may also be arranged substantially in the middle between the two opposing sides of the bioreactor bag. The bioreactor bag is formed from transparent or semi transparent material so that the interior of the bioreactor bag is visible. This is advantageous since the harvesting process can be observed. It is noted that the longitudinal axis and the width direction of the harvesting device correspond to the longitudinal axis and the width direction of the harvesting device when the bioreactor bag is fixed to the harvesting device.

The harvesting device comprises a base. The base may be formed as a substantially planar plate, such as a bed plate, for example. The base is configured such that it can be arranged in a predetermined manner with respect to a horizontal plane.

The harvesting device, particularly the base thereof, may be configured such that two or more harvesting devices may be stacked on top of each other with substantially no or very little space in the vertical direction between the harvesting devices in the stacked state. This allows storing multiple harvesting devices with minimum required space when the harvesting devices are not in use.

The harvesting device further comprises a first and a second fixing device. The fixing devices are configured to fix the fixing portions of the bioreactor bag to the harvesting device. The first fixing device can fix the first fixing portion and the second fixing device can fix the second fixing portion, preferably the first fixing device can fix the first fixing portion by means of the first thickened portion and the second fixing device can fix the second fixing portion by means of the second thickened portion. In this respect, the term "fixing" is to be understood such that the first and second fixing portions may be removably attached to the first and second fixing devices of the harvesting device. The first and second fixing devices are designed to position the bioreactor bag in a predetermined or predeterminable position on the harvesting device, so that the bioreactor bag is arranged in a manner that the surface of the bioreactor bag comprising the harvesting port faces downward, for example toward the upper surface of the base, for removal of the content of the bioreactor bag. The surface of the bioreactor bag comprising the harvesting port may also be referred to as the "removal surface" or "removal side" of the bioreactor bag.

The harvesting device further comprises an adjusting device. The adjusting device is configured to adjustably fix the arrangement of one of the fixing portions, e.g., the first fixing portion or the second fixing portion, relative to the base. The adjusting device may also be configured to adjustably fix both fixing portions, i.e., the first and the second fixing portions, relative to the base. The adjusting device can be configured to adjustably fix the arrangement of the two fixing portions, e.g., the first and the second fixing portion, with respect to the base independently from each other or at the same time. The adjusting device may therefore adjust the location of the fixing devices relative to the base in order to position the bioreactor bag after fixing of the fixing portions to the fixing devices. When in an arrangement in the center of an adjusting range of the first fixing device and the second fixing device, the distance of the first fixing device to the base may be smaller than the distance of the second fixing device to the base, or vice versa.

The fixing devices may be detachably coupled to the adjusting device, which may simplify fixing the bioreactor bag to the harvesting device. In particular, such a configuration enables to fix the fixing devices to the bioreactor bag while it is still placed on the bioreactor device, and the bioreactor bag with the fixing devices attached thereto can then be transferred to the harvesting device. The pre-fixed fixing devices can then be attached to the harvesting device by clipping, sliding, magnets or other suitable means.

The harvesting device can be made of various material including, but not limited to, plastic, metal and/or other suitable material.

The content of the bioreactor bag can be a liquid or a suspension. The bioreactor bag can furthermore contain a gas or gases. The content of the bioreactor bag may be mixed or circulated by means of a moving device, as a result of which good oxygen mixing can be ensured in particular during the cell cultivation. After the moving or mixing process, the bioreactor bag may be removed from the moving device and may be arranged and fixed in the harvesting device for harvesting the content of the bioreactor bag. For this purpose, the fixing portions of the bioreactor bag are fixed with the fixing devices so that the bioreactor bag hangs between the two fixing devices and the removal surface of the bioreactor bag faces downward, for example toward the upper surface of the base. The fixing devices may be arranged such that the bioreactor bag is allowed to hang freely there between, even with the bioreactor bag having a substantial sag, without contacting the base or the floor on which the harvesting device is placed. By means of the adjusting device, the arrangement of the bioreactor bag relative to the base, and particularly relative to the horizontal plane, may be optimized. In particular, by changing the position or arrangement of the fixing devices, the harvesting port may be positioned substantially at the lowermost point of the bioreactor bag. This lowermost point of the bioreactor bag is preferred, so that harvesting, draining or transfer of the content of the bioreactor bag is enabled by means of gravity. Due to the gravitational force, the content of the bioreactor bag consequently leaves the bioreactor bag in an advantageous manner. In this way, the content of the bioreactor bag is harvested in a simplified manner, wherein at the same time a residual volume remaining in the bioreactor bag after the harvesting process is reduced so that the entrapped dead volume remaining in the bioreactor bag after the harvesting process is minimized. It is noted that it is also possible to pressurize the bioreactor bag to help push the content of the bioreactor out through the harvesting port. It is further noted that before and during harvesting, it is preferable to close all other ports in order to prevent any liquid, cells and/or gases to enter other lines and ports.

According to the invention, gravity enables the harvesting with only minimal operator interaction. The harvest device works with any kind of top port by simply turning the bioreactor bag upside down in order to place the harvesting port to the lowest point during draining. In case of a bottom port, there would be no need to turn the bioreactor bag upside down.

Preferably, the harvesting device is free of any moving device for moving the bioreactor bag and/or any tempering device for tempering the bioreactor bag.

A moving device according to the present application refers to any driven or motorized device for moving the bioreactor bag so as to move and/or mix the content of the bioreactor bag during cell cultivation. The moving device may be a rocker, for example. The processes of cultivation and of harvesting the content of the bioreactor bag can be decoupled into separate phases. In particular, after mixing and tempering the substances in the bioreactor bag, it can be removed from the bioreactor device and moved into the harvesting device for harvesting the content of the bioreactor bag as described above. Thus, the harvesting device may be completely decoupled from the bioreactor device, and thus from the mixing and tempering device, so that the bioreactor is not blocked during the harvesting process and can be immediately prepared for the next cultivation during harvesting of the content of the bioreactor bag. The effectiveness of the cultivation process of the bioreactor is significantly increased. The location of the harvesting device can be completely decoupled from the bioreactor, so that the bioreactor bag can be removed from the bioreactor device and can be transported to the location of the harvesting device. The harvesting device may also be transported to the bioreactor device or bioreactor bag. Thus, the bioreactor bag can be harvested in a spatially flexible manner.

Preferably, the first fixing device and/or the second fixing device comprises a clamp configured to clamp the fixing portions substantially along the width thereof.

In order to position or fix the bioreactor bag on the first fixing device and the second fixing device, the fixing devices can comprise clamps. The clamps may comprise clamping rails, -rods or -plates, for example, which may be displaced towards each other to clamp the respective fixing portion there between. The clamping rails, -rods or -plates may also be fixedly arranged with respect to each other, forming an open slot into which the respective fixing portion may be slid into from the side, i.e. in the width direction of the bioreactor bag, so that a thickened portion of the fixing portion is clamped or held between the clamping rails, -rods or -plates. The configuration of the fixing devices as clamps is advantageous, since a detachable positioning or fixing of the bioreactor bag on the fixing device and thus in the harvesting device can be achieved in a simple manner. Each of the clamps of the fixing devices can be formed so that the slot or space formed within the clamp substantially along the width thereof extends in a plane that is substantially parallel to a horizontal plane, preferably substantially parallel to the upper surface of the base. Thus, it is possible to introduce the fixing portions of the bioreactor bag into the slots or spaces in a simplified manner so that the bioreactor bag is fixed with the fixing device. The bioreactor bag may be slid into the slot or space in the clamps from the side or from the top and is held in place using the fixing portions on the bioreactor bag which are used for fixation on the harvesting device. The slot or space in the clamps may extend between an open end of the clamps and a closed end of the clamps. Thus, the fixing portions may be easily introduced into the clamp via the open end and may not slip out of the slot or space at the closed end. On the other hand, the closed end prevents the fixing portions from slipping out of the slot or space and contributes to a secure fixing of the fixing portions. Thus, the harvesting process is further improved. It is noted that the orientation of the open ends of the clamps is flexible, so that the bioreactor bag may be inserted from the left or right of the harvesting device depending on the set up of the harvesting device (i.e. by rotating the harvesting device 180° about a vertical axis). In case detachable fixing portions are provided, said detachable fixing portions may be configured such that they can be attached in the harvesting device in different arrangements which are rotated 180° with respect to each other, which further simplifies orienting the open ends of the clamps in a desired manner.

Preferably, the base comprises a stand for placing the harvesting device on a substantially horizontal surface.

The stand can be integrally formed with a main body of the base, wherein the main body of the base is preferably a substantially plate shaped member. It is also possible that the stand is connected to the main body of the base in a detachable manner. The stand is preferably located on a lower surface of the main body of the base opposing to the upper surface. However, the stand may also be located at any other surface of the main body of the base. In the present application, positional or directional indications such as "upper", "lower", "up", "down" or the like relate to a state in which the harvesting device is arranged for actual use with respect to a horizontal plane. The stand may comprise at least two support members that are attached to the lower surface or integrally formed with the lower surface of the main body of the base preferably at two opposing peripheral regions of the main body of the base. The support members can extend from the lower surface of the main body of the base with an angle of 90°. The support members can be formed to have an elongated shape, round shape, triangle shape or any other shape. However, the stand may also be formed as a plate that extends in a horizontal plane that is distant from the lower surface of the main body of the base, preferably in a plane parallel to the main body of the base. This plate may be integrally formed or connected with the main body of the base. Thus, the harvesting device can be placed on a carrier, e.g., a table or a lab bench, or on the floor, in a sufficiently stable manner so that the position of the harvesting port at the lowermost point of the bioreactor bag can be easily achieved. In this way, the content of the bioreactor bag is harvested in a simplified manner, wherein at the same time a residual volume remaining in the bioreactor bag after the harvesting process is reduced, and wherein, preferably, the entrapped dead volume remaining in the bioreactor bag after the harvesting process is minimized.

Preferably, the base comprises an attaching mechanism to attach the harvesting device to a frame structure.

The attaching mechanism may be formed as a clamp which allows the harvesting device to be attached to the frame structure. The clamp may comprise a screw which may be manually tightened for attachment to the frame structure. The frame structure can be any conventional frame structure such as ones used in labs for attaching equipment thereto. The frame structure may be placed or fixed to the floor, fixed to the wall or placed or fixed to a carrier, such as a table or a lab bench. However, it is also possible to attach the harvesting device via the attaching mechanism directly to the table or a lab bench, e.g., to an edge region of a table plate or a lab bench plate.

The attaching mechanism allows the attachment of the harvesting device to any desired location of a frame structure so that a user can fix the bioreactor bag with the harvesting device in a convenient manner, e.g., while standing or sitting. This enables a precise adjustment of the harvesting point at the lowermost point of the bioreactor bag, so that harvesting, draining or transfer of the content of the bioreactor bag is enabled by means of gravity.

Preferably, the adjusting device comprises a tilting mechanism for tilting the first fixing device and/or the second fixing device with respect to the base.

The tilting mechanism can be configured so that the first and second fixing devices may be freely tilted or rotated with respect to the base, so that the arrangement of the bioreactor bag attached to the first and second fixing devices can be adjusted in a desired manner. Accordingly, regardless of the position of the harvesting port on the bioreactor bag, the bioreactor bag can be arranged in the harvesting arrangement in which the harvesting port is positioned substantially at the lowermost point of the bioreactor bag. The tilting mechanism may comprise a spherical joint or hinge joint.

The adjusting device or the tilting mechanism can comprise a lock in order to fix the tilted fixing devices at a preferred position. This lock can be formed as a screw engaging with the joint of the tilting mechanism which may be manually tightened. The lock may also be formed as a scale. This allows a convenient adjustment and reproduction of the preferred position of the harvesting device and the fixing of the harvesting device after having achieved the desired tilted position.

Preferably, the tilting mechanism comprises only one rotary degree of freedom.

The first and/or second fixing device can be tilted or rotated by means of the tilting mechanism about a predetermined tilt axis. The tilt mechanism may comprise a hinge joint, wherein the tilt axis of the hinge joint may be substantially parallel to the horizontal plane and may also be substantially parallel to the first and/or second fixing devices. More specifically, the tilt axis may extend substantially parallel to the slots or spaces within each of the fixing devices. Thus, after the bioreactor bag has been fixed with the fixing devices of the harvesting device, e.g., by sliding the fixing portions into the clamps, the harvesting device may be tilted around the tilt axis by means of the tilting mechanism. This enables an improved and simple adjustment of the harvesting port at the lowermost point after the bioreactor bag has been fixed to the fixing devices, so that harvesting, draining or transfer of the content of the bioreactor bag is enabled by means of gravity, particularly when the harvesting port is arranged on the longitudinal axis (centerline) of the bioreactor bag. In this way, a residual volume remaining in the bioreactor bag after the harvesting process is reduced so that the entrapped dead volume remaining in the bioreactor bag after the harvesting process is minimized.

Preferably, the adjusting device comprises a holding arm, wherein one end of the holding arm is connected to the base and the other end of the holding arm is connected to the first fixing device or the second fixing device, and wherein the holding arm is configured such that the length thereof can be adjusted.

The holding arm can be arranged on: the upper surface of the base. The holding arm can be integrally formed with the base or can be connected with the base, so that a first end of the holding arm is connected to the base and an opposing second end extends away as a free end distant from the base. The holding arm may be formed as a two-piece element comprising a first rod element and a second rod element. The first and second rod elements may be formed as elongated rod elements having a cross-section with respect to their longitudinal axis of a particular geometrical form, e.g., a circular cross-section, a triangular cross-section, or a rectangular cross-section, etc. Preferably, the first rod element has a cross-section with respect to its longitudinal axis with an outer diameter that is smaller than the diameter of the cross-section of the second rod element so that the second rod element can be moved over the first rod element so that the first rod element extends at least partly in the interior of the first rod element. For example, a first end of the first rod element can be connected with the base of the harvesting device, preferably the upper surface of the base, and an opposing, second end of the first rod element can be introduced into a first end of the second rod element. A second end of the second rod element opposing to the first end of the second rod element may be connected with the first fixing device or the second fixing device. Based on this configuration of the holding arm, the distance of the first fixing device is adjustable with respect to the base of the harvesting device. This in turn allows an optimized adjustment of one of the fixing portions of the bioreactor bag that have been fixed with the fixing devices so that the harvesting port is located at the lowermost point of the bioreactor bag. An optimized harvesting, draining or transfer of the content of the bioreactor bag by means of gravity is enabled. In this way, a residual volume remaining in the bioreactor bag after the harvesting process is reduced so that the entrapped dead volume remaining in the bioreactor bag after the harvesting process is minimized.

The holding arm can comprise a lock in order to fix the first and the second rod elements with respect to each other when the first rod element extends at least partly within the second rod element. This lock can be formed as a bolt that penetrates a through-hole within the outer walls of the second rod element in order to engage with the outer wall of the first rod element that extends at least partly within the second rod element at the desired position.

It is also possible that the diameter of the first rod element that is connected with the base is larger than the diameter of the second rod element so that the second rod element may be introduced into the first rod element in order to adjust one of the fixing portions of the bioreactor bag that have been introduced into the fixing device so that the harvesting port agrees with the lowermost point of the bioreactor bag. In this configuration, the lock can be formed as a bolt that penetrates a through-hole within the outer wall of the first rod element in order to engage with the outer wall of the introduced second rod element at the desired position.

The lock may also comprise a screw engaging the first and second rod elements, which can be tightened manually for locking.

Preferably, the adjusting device comprises two holding arms, wherein the other ends of the holding arms are connected to the first fixing device and the second fixing device, respectively.

The harvesting device can comprise a first holding arm and a second holding arm, wherein both holding arms can be arranged on the upper surface of the base. Each of the first and second holding arms may be configured as described above. Thus, each of the first and second holding arms may be formed as a two-piece element comprising a first rod element and a second rod element as described above. A first end of the first rod elements of the first and second holding arms can be connected with the base of the harvesting device, preferably the upper surface of the base, and an opposing, second end of the first rod element can be introduced into a first end of the second rod elements of the first and the second holding arms. A second end of the second rod element of the first holding arm opposing to the first end of the second rod element is connected with the first fixing device. A second end of the second rod element of the second holding arm opposing to the first end of the second rod element is connected with the second fixing device. Based on this configuration of the first and the second holding arms the distance of the first fixing device and of the second fixing device is adjustable with respect to the base of the harvesting device. Thus, the distance of the first fixing device to the base may be adjusted in order to be equal to the distance of the second fixing device to the base. However, the distance of the first fixing device to the base may also be adjusted in order to be larger or smaller than the distance of the second fixing device to the base. This allows an optimized adjustment of the fixing portions of the bioreactor bag that have been introduced into the fixing device so that the harvesting port agrees with the lowermost point of the bioreactor bag. An optimized harvesting, draining or transfer of the content of the bioreactor bag by means of gravity is enabled.

Preferably, the first holding arm is positioned at a peripheral region of the upper surface of the base and the second holding arm is positioned at another peripheral region of the upper surface that is distinct from the first peripheral region. Preferably, the holding arms are positioned at opposing peripheral regions along the longitudinal axis of the base. The fixing portions of the bioreactor bag can be introduced into the fixing devices of the harvesting device wherein the bioreactor bag hangs between the first and second holding arms, wherein the harvesting port may be adjusted so that the lowermost point of the bioreactor bag faces toward the base. There is also enough space between the harvesting port and the upper surface of the base for convenient draining and/or removal of the content of the bioreactor bag, e.g., for conduits to transport the content into a target bag placed on a table or lab bench.

Each of the first and second holding arms can comprise a lock as described above.

Preferably, the second rod elements are connected with the first rod elements, e.g. in that the second rod elements are moved over the first rod elements or vice versa, so that the open ends of the clamps face into the same direction. Thus, the two fixing portions are introduced into the fixing devices from the same direction. However, at least one of the second rod elements may also be connected with the first rod element so that the two open ends of the clamps face into opposing directions. Thus, the two fixing portions are introduced into the fixing devices from opposite directions. This further contributes to the adjustment of the harvesting port agreeing with the lowermost point of the bioreactor bag.

Preferably, the first and second fixing devices are connected to each other by a connecting structure, wherein the connecting structure is connected to the adjusting device.

The connecting structure can be connected coupled to the base, preferably to the upper surface of the base, via the adjusting device. The connecting structure can be integrally formed with the first and second fixing devices.

This configuration allows an easy adjustment of the arrangement of both fixing portions at the same time. An optimized harvesting, draining or transfer of the content of the bioreactor bag by means of gravity is enabled. In this way, a residual volume remaining in the bioreactor bag after the harvesting process is reduced so that the entrapped dead volume remaining in the bioreactor bag after the harvesting process is minimized.

Preferably, the connecting structure has a substantially concave shape in cross section, wherein the concave shape opens upward in the harvesting arrangement.

The connecting structure can have a concave shape or U-shape in cross section perpendicular to the width direction of the harvesting device. More specifically, the connecting structure may comprise a first uprising portion and a second uprising portion, wherein an upper end of the first uprising portion is connected to the first fixing device and an upper end of the second uprising portion is connected to the second fixing device. The lower ends of the first and second uprising portions may be connected via a bridging portion. The first uprising portion, the second uprising portion and/or the bridging portion may be substantially plate shaped. The concave shape can be symmetrical in cross section so that the concave shape has a lowermost, minimum location and two uprising portions extending away from the minimum with the same curvature and each having a free end. However, it is also possible that the concave shape is non-symmetrical in cross section so that the two uprising portions extend away from the minimum with a different curvature and/or length. The connecting structure can be integrally formed as a through or a bowl, wherein the two uprising portions are integrally formed with the bridging portion. It is also possible that the connecting structure is a sheet that is arcuated in a concave manner.

This allows a convenient fixing of the fixing portions of the bioreactor bag into the fixing devices of the connecting structure so that the bioreactor bag hangs between the two uprising portions. By such a configuration the harvesting port can be adjusted so that the lowermost point of the bioreactor bag faces toward the base. There is also enough space between the harvesting port and the upper surface of the base for convenient draining and/or removal of the content of the bioreactor bag, e.g., for conduits to transport the content into a target bag placed on a table or lab bench.

Preferably, the connecting structure comprises a pivoting mechanism allowing the first and second fixing devices to be pivotable between the harvesting arrangement and a fixing arrangement for fixing the bioreactor bag to the harvesting device, independently from the adjusting device.

The connecting structure can be coupled to the adjusting device by means of the pivoting mechanism. The pivoting mechanism may comprise a hinge joint having a pivot axis which may be perpendicular to the tilt axis of the adjusting mechanism, for example. In particular, the pivot axis may be parallel to the longitudinal axis of the harvesting device and extend along the longitudinal axis of the harvesting device in plan view. The connecting structure may be pivoted about the pivot axis in a range of between about 0° and about 180°. In the fixing arrangement, the first and second fixing devices are preferably pivoted about 90° about the pivot axis with respect to the harvesting arrangement, so that the fixing portions of the bioreactor bag can be simply slid into the fixing devices in a vertical direction downward. However, in the fixing arrangement, the first and second fixing devices may also be pivoted about 180° about the pivot axis with respect to the harvesting arrangement, so that the bioreactor bag may lie on a planar portion of the connecting structure with the surface including the harvesting port facing upward, which also simplifies the fixing of the bioreactor bag to the harvesting device.

The first and second fixing devices can be pivoted about the pivot axis between the harvesting arrangement and a fixing arrangement. In the fixing arrangement, the connecting structure may be in a first position, wherein the first and second fixing devices may extend in a plane that is transverse to a substantially planar portion of the pivoting mechanism, so that the plane including the first and second fixing devices is pivoted with respect to the substantially planar portion of the pivoting mechanism preferably in an angle of about 180° or about 90°. The first position of the connecting structure allows a convenient fixing of the bioreactor bag with the first and second fixing devices so that the fixing portions of the bioreactor bag can be easily introduced into the fixing portions.

The connecting structure can be pivoted about pivot axis from the first position into a second position so that the first and second fixing devices are pivoted into the harvesting arrangement. In the second position, the first and second fixing devices may extend in a plane that is substantially parallel to the substantially planar portion of the pivoting mechanism, so that the plane including the first and second fixing devices and the substantially planar portion of the pivoting mechanism preferably include an angle that is about 0° with respect to each other. The second position of the connecting structure allows the bioreactor bag hanging between the first fixing device and the second fixing device with the harvesting port being positioned substantially at the lowermost point of the bioreactor bag.

The pivoting mechanism can be connected with the adjusting device so that the connecting structure is tiltable about the tilt axis.

The pivoting mechanism can comprise a first projecting element and the adjusting device can comprise a second projecting element. The first projecting element may be formed as a flat element protruding downward from the substantially planar portion of the pivoting mechanism and the second projecting element may be formed as a flat element connected in a fixed manner with the base while protruding upward from the base. Preferably, the two projecting elements are connected with each other in such a manner that the first projecting element may abut against the second projecting element. During pivoting about the tilt axis, a surface of the first projecting element may slide along a surface of the second projecting element.

Thus, after a fixing of the fixing portions of the bioreactor bag with the fixing devices of the harvesting device in the fixing arrangement, the connecting structure can be pivoted around the pivot axis from the first position into a second position in the harvesting arrangement so that the bioreactor bag hangs between the first fixing device and the second fixing device. In the harvesting arrangement, the connecting structure can be pivoted around the tilt axis so that the harvesting port is positioned substantially at the lowermost point of the bioreactor bag.

The pivoting mechanism can comprise a lock in order to fix the pivoted connecting structure at a preferred position about the pivot axis. This lock can be formed as a lever element for manually tightening a locking screw. The lock of the pivoting mechanism may be formed as a scale.

Preferably, the harvesting device further comprises a stacking aid, wherein the stacking aid is configured to be detachably mounted to a mounting portion of the harvesting device such that another harvesting device can be arranged and stacked in a stacking arrangement with the harvesting device, and wherein the stacking aid is configured to prevent a lateral displacement of the harvesting devices relative to each other in the stacking arrangement.

The stacking aid is configured to be connected or to be connectable to a mounting portion of the harvesting device so that a second or another harvesting device can be arranged and stacked onto the harvesting device in a stacking arrangement. This is advantageous, since due to the means of the stacking aid the harvesting devices may be easily arranged and stacked so that the storing place is reduced.

The mounting portion can be any portion of the harvesting device that is suitable for mounting the stacking aid so that the harvesting devices may be arranged and stacked. For example, the mounting portion of the harvesting device can be a portion of the base, particularly a portion of the stand or the attaching mechanism, a portion of the adjusting device, particularly a portion of a holding arm, or a portion of the connecting structure.

Preferably, the mounting portion is arranged at a portion of a holding arm comprising an operating element of said holding arm, as this facilitates mounting of the stacking aid to the harvesting device. In particular, the mounting portion may be arranged at the later described first lock and/or at the second lock of the harvesting device, the first and second locks being configured to fix the first rod elements and the second rod elements of each of the holding arms of the harvesting device to each other. More particularly, the stacking aid can be configured to be connectable or to be detachably mountable to the first bolt of the first lock and/or the second bolt of the second lock of the harvesting device. This is advantageous, since the first and second bolts are easily accessible for the user from a lateral portion of the harvesting device. At the same time, the connection or detachable mounting of the mounting portion at one of the first and second bolts allows an arrangement and stacking of the second or another harvesting device with the (first) harvesting device. Thus, the user may arrange and stack at least two harvesting devices one upon the other. In the stacking arrangement, the bases of the harvesting devices can be arranged substantially parallel to each other.

However, it is also possible to configure the stacking aid so that the stacking aid can be connectable or detachably mountable with a mounting portion that is different from the first bolt of the first lock and/or the second bolt of the second lock. As an example, the mounting portion may also be located at the base of the harvesting devices, so that the stacking aid is connected or detachably mounted around a peripheral edge of the base adjacent to the upper surface of the based and the lower surface of the base.

The stacking aid may prevent lateral displacement of the harvesting devices relative to each other in the stacking arrangement by establishing a form fit in the lateral direction with respect to a portion of the harvesting device, particularly the later described holding portion of the harvesting device. The stacking aid may be configured such that, in the stacking arrangement, a portion of an above harvesting device may rest on a portion of a below harvesting device. Alternatively, the stacking aid may be configured such that, in the stacking arrangement, a lower edge of a stacking aid of an above harvesting device rests on an upper edge of a stacking device of a below harvesting device.

Preferably, the stacking aid comprises a first lateral portion and a second lateral portion, wherein the first and second lateral portions are arranged on opposing lateral sides of a stacking aid longitudinal axis, and wherein at least one of the first and second lateral portions comprises a mounting recess configured to at least partly receive the mounting portion of the harvesting device, so as to fix the stacking aid to the harvesting device in the longitudinal direction and in the lateral direction. The lateral direction of the stacking aid is transverse or perpendicular to the stacking aid longitudinal axis or direction and may correspond to the lateral direction of the harvesting device.

The stacking aid is configured to extend along the stacking aid longitudinal axis, wherein opposing ends of the stacking aid in the direction of the stacking aid longitudinal axis may be opened in the longitudinal direction and a height direction perpendicular to the longitudinal and lateral directions of the stacking aid. At the open ends in the stacking aid longitudinal direction, the stacking aid may have a substantially C-shaped cross section.

Opposing ends of the stacking aid in the lateral direction are formed by a first lateral portion and a second lateral portion. The open ends in the stacking aid longitudinal direction allow an easy mounting to the harvesting device, wherein particularly, the open ends allow the reception of the first holding arm in the vicinity of the first lock and/or the reception of the second holding arm in the vicinity of the second lock. Thus, in the stacking arrangement, the stacking aid may be mounted to the mounting portion such that the first holding arm or the second holding arm extends along the stacking aid longitudinal axis between the opposing open ends and beyond the opposing open ends. The first lateral portion and the second lateral portion may abut against opposing lateral edges or surfaces of the first holding arm or the second holding arm, such that a form fit is established and the stacking aid is fixed to the harvesting device in the lateral direction.

The first and second lateral portions can be substantially plate-shaped. The stacking aid may be formed from a sheet or plate material, particularly from a sheet metal. This is advantageous, since it enables simple and cost efficient manufacturing. At the same time, the first and second lateral portions may be easily adapted to the arrangement of the mounting portion of the harvesting device. The metal of the stacking aid may be steel or aluminum, for example.

At least one of the first and second lateral portions can comprise a mounting recess. The mounting recess can extend from an edge of at least one of the first and second lateral portions at least partially within the at least one lateral portion in a direction substantially traverse or perpendicular to the stacking aid longitudinal axis, i.e. substantially in the height direction of the stacking aid. Thus, the mounting recess can extend between a first, open end in the vicinity of the edge of the at least one of the first and second lateral portion and a second, closed end. The mounting recess, in the longitudinal direction, may be arranged in a portion of the first and/or second lateral portion between the open ends of the stacking aid in the longitudinal direction, particularly substantially in the center between the open ends of the stacking aid in the longitudinal direction.

The second, closed end of the mounting recess may be semi-circularly formed and may have a diameter which is at least as large as the diameter of the first bolt of the first lock and/or the second bolt of the second lock. Preferably, the diameter of the second, closed end of the mounting recess has a diameter which is substantially as large as the diameter of the first bolt and/or the second bolt. This allows an easy and secure mounting of the stacking aid to the mounting portion of the harvesting device, and enables fixing the stacking aid to the harvesting device at least in the longitudinal direction by means of a form fit. In particular, the stacking aid may be arranged around the first bolt and/or the second bolt of the locks of the adjusting device, wherein the stacking aid may be placed around the first or second holding arm in the vicinity of the first or second lock, so that the first or second bolt can be received by the mounting recess. In the stacking arrangement, the first bolt or the second bolt may abut against the second, closed end of the mounting recess, so as to establish a form fit. In other words, the first bolt or the second bolt can engage with the mounting recess, particularly with the second, closed end of the mounting recess, to fix the stacking aid to the harvesting device.

Preferably, the mounting recess comprises opposing rounded edges in the vicinity of the first, open end. The opposing rounded edges are located on opposing sides in the mounting recess longitudinal axis. The rounded edges allow an easy introduction of the first bolt or the second bolt into the mounting recess and an easy reception of the first bolt or the second bolt in the mounting recess.

Preferably, the first lateral portion comprises a first mounting recess and the second lateral portion comprises a second mounting recess. Each of the first and second mounting recesses may be formed as described above. The first and second mounting recesses may be formed substantially identically with respect to each other, so that a secure arrangement of the stacking aid does not depend on the exact arrangement of the opposing, open ends of the stacking aid in the direction of the stacking aid longitudinal axis. In other words, both the first mounting recess and the second mounting recess may receive the first or second bolt of the holding arm in order to securely arrange the stacking aid with the harvesting device.

Preferably, the first lateral portion comprises a first protrusion and the second lateral portion comprises a second protrusion, wherein the first and second protrusions protrude substantially in a height direction perpendicular to the stacking aid longitudinal axis and the lateral direction substantially parallelly to each other. The first and second protrusions can be configured to hold a holding portion of the harvesting device in the stacking arrangement.

The first and second protrusions can extend in the same direction relative to the stacking aid longitudinal axis. The first protrusion can protrude from an edge of the first lateral portion and the second protrusion can protrude from an edge of the second lateral portion in a direction away from the lateral portions and away from the first mounting recess and/or second mounting recess. The first protrusion can extend around a protrusion longitudinal axis which extends in the same plane as the mounting recess longitudinal axis of the first lateral portion, wherein, preferably, the protrusion longitudinal axis and the mounting recess longitudinal axis extend along a common straight line within the plane. The second protrusion can extend around a protrusion longitudinal axis which extends in the same plane as the mounting recess longitudinal axis of the second lateral portion, wherein, preferably, the protrusion longitudinal axis and the mounting recess longitudinal axis extend along a common straight line within the plane.

The holding portion can be any portion of the harvesting device that is suitable for being held by the stacking aid so that a lateral displacement of the harvesting devices relative to each other may be prevented. For example, the holding portion of the harvesting device can be a portion of the base, particularly a portion of the stand or the attaching mechanism, a portion of the adjusting device, particularly a portion of a holding arm, or a portion of the connecting structure.

The first and second protrusions can be substantially plate-shaped. Preferably, the stacking aid including the first and second protrusions is formed from a sheet or plate material, particularly from a sheet metal. The first and second protrusions can extend from the edges of the first and second lateral portions, respectively. In particular, the first and second protrusions may extend in the same plane as the first and second lateral portions. In the stacking arrangement, the first and second protrusions overlap with the holding portion of the harvesting device in the lateral direction, so as to establish a form fit. In other words, the stacking aid can engage with the harvesting device, e.g., with the holding arms of the harvesting device, so as to establish a lateral form fit by the protrusions. The first and second protrusions are advantageous, since they prevent a lateral displacement of the second or another harvesting device relative to the (first) harvesting device in the stacking arrangement in a simple manner. In particular, when the second harvesting device is arranged and stacked onto the (first) harvesting device by means of the stacking aid, the first and second protrusions can abut against the side surfaces of the holding arms of the harvesting devices. In the stacking arrangement, inner surfaces of the first and second protrusions, which face the holding arm arranged there between, can abut against opposing side surfaces of the holding arms, wherein at one of these side surfaces, the lock comprising the bolt may be located. Thus, the first and second protrusions can be configured to hold a holding portion of the harvesting device in the stacking arrangement. The holding portion can be formed by the opposing side surfaces of the holding arms.

Preferably, the stacking aid is formed substantially plane symmetrically.

The stacking aid can be formed substantially plane symmetrically with respect to a symmetry plane including the stacking aid longitudinal and height directions. In particular, the first lateral portion and the second lateral portion can be arranged parallel to each other in the lateral direction and parallel to the symmetry plane. Furthermore, the first and second mounting recesses can be formed within the first and second lateral portion, respectively, so that the recesses are arranged parallel to each other and have identical shapes and/or dimensions. In addition, the first and second protrusions can be formed from the edges of the first and second lateral portions, respectively, wherein the first and second protrusions are parallel to each other in the lateral direction and parallel to the symmetry plane. This configuration allows an easy manufacturing of the stacking aid, particularly since the same stacking aid may be used for the first holding arm and the second holding arm, for example.

Preferably, the first and second lateral portions are connected to each other by a first connecting portion, particularly a first connecting sheet, and a second connecting portion, particularly a second connecting sheet, which extend between the first and second lateral portions, respectively. The first connecting portion and the second connecting portion may be arranged at the open ends of the stacking aid in the stacking aid longitudinal direction, respectively. The first and second protrusions may be arranged, particularly centrally, between the first and second connecting portions in the stacking aid longitudinal direction. The first and second connecting portions can be arranged parallel to each other in the stacking aid longitudinal direction. The stacking aid can comprise an opening between the first connecting portion and the second connecting portion, wherein the first and second protrusions and said opening may be formed by bending up a portion of the sheet material corresponding to said opening. The stacking aid may thus be easily formed from a sheet material, e.g., a sheet metal, wherein the mounting recesses may be cut out from opposing sides of the row sheet and wherein the first and second protrusions may be cut out from an area in-between the two mounting recesses and bent. Thus, the stacking aid may be formed by folding or bending a sheet material about a first and second folding axis which may extend parallel to each other and parallel to the stacking aid longitudinal axis or direction.

Preferably, the harvesting device comprises two stacking aids.

The harvesting device can comprise a first stacking aid and a second stacking aid, wherein each of the first and second stacking aids can comprise some or all the features and advantages as described above. Thus, the first stacking aid can be configured to be detachably mounted to a first mounting portion and the second stacking aid can be configured to be detachably mounted to a second mounting portion. The first stacking aid may be arranged around the first holding arm in the vicinity of the first lock, so that the first bolt can be received by one of the mounting recesses of the first stacking aid. The second stacking aid may be arranged around the second holding arm in the vicinity of the second lock, so that the second bolt can be received by one of the mounting recesses of the second stacking aid. Thus, the first stacking aid prevents a lateral displacement of the first holding arm of the second or another harvesting device in the stacked arrangement and the second stacking aid prevents a lateral displacement of the second holding arm of the second or another harvesting device in the stacked arrangement. The first and second stacking aids allow an improved stacking and arrangement of the second or another harvesting device on the (first) harvesting device.

Preferably, the harvesting device comprises up to four stacking aids, more preferably, the harvesting device comprises up to eight stacking aids.

By means of the stacking devices as described above, up to four or even more harvesting devices may be arranged in a stacking arrangement onto each other. Two stacking aids may be detachably mounted to a first and second mounting portion of each of the four harvesting devices, respectively. The second harvesting device can be arranged and stacked onto the (first) harvesting device in a stacking arrangement, the third harvesting device can be arranged and stacked onto the second harvesting device in a stacking arrangement, and the fourth harvesting device can be arranged and stacked onto the third harvesting device in a stacking arrangement. Thus, two stacking aids may be detachably mounted to the mounting portions of the first harvesting device, e.g., the first and second bolts of the holdings arms of the first harvesting device may be received by respective mounting recesses of the stacking aids. At the same time, a form fit in the lateral direction with respect to the holding portion of the second harvesting device may be established. The holding portion of the second harvesting device may comprise opposing side surfaces of the holding arms of the second harvesting device. The protrusions of the stacking aids detachably mounted to the mounting portions of the first harvesting device may hold the opposing side surfaces of the holding arms of the second harvesting device thus preventing a lateral displacement. In the same manner, two stacking aids may be detachably mounted to the mounting portions of the second harvesting device, e.g., the first and second bolts of the holdings arms of the second harvesting device may be received by respective mounting recesses of the stacking aids. At the same time, a form fit in the lateral direction with respect to the holding portion of the third harvesting device may be established. The holding portion of the third harvesting device may comprise opposing side surfaces of the holding arms of the third harvesting device. The protrusions of the stacking aids detachably mounted to the mounting portions of the second harvesting device may hold the opposing side surfaces of the holding arms of the third harvesting device thus preventing a lateral displacement. Finally, two stacking aids may be detachably mounted to the mounting portions of the third harvesting device, e.g., the first and second bolts of the holding arms of the third harvesting device may be received by respective mounting recesses of the stacking aids. At the same time, a form fit in the lateral direction with respect to the holding portion of the fourth harvesting device may be established. The holding portion of the fourth harvesting device may comprise opposing side surfaces of the holding arms of the fourth harvesting device. The protrusions of the stacking aids detachably mounted to the mounting portions of the third harvesting device may hold the opposing side surfaces of the holding arms of the fourth harvesting device thus preventing a lateral displacement.

In the stacking arrangement, lower edges of the lateral portions of the stacking aids of the second harvesting device may abut against the upper edges of the lateral portions of the stacking aids of the first harvesting device. The upper edges refer to the edges of the lateral portions which are above the mounting recess and, thus, above the protrusions in the stacking arrangement, and the lower edges refer to the edges of the lateral portions which are below the mounting recess and, thus, below the protrusions in the stacking arrangement. Here, "above" and "below" are to be understood with respect to a vertical direction of the harvesting device(s) in the stacking arrangement. Furthermore, in the stacking arrangement, the lower edges of the lateral portions of the stacking aids of the third harvesting device can abut against the upper edges of the lateral portions of the stacking aids of the second harvesting device. In the stacking arrangement, the lower edges of the lateral portions of the stacking aids of the fourth harvesting device can abut against the upper edges of the lateral portions of the stacking aids of the third harvesting device. Thus, the harvesting devices may rest stably on each other in the stacking arrangement.

The stacking aid as described in the present application is an aspect of the present invention.

According to the present invention, a system for harvesting a content of a bioreactor bag is provided, the system comprising: a bioreactor bag having fixing portions at both longitudinal ends thereof and a harvesting port for draining the content of the bioreactor bag provided between said longitudinal ends, and the harvesting device of any one of claims 1 to 12.

The bioreactor bag and the harvesting device, which are part of the system for harvesting a content of a bioreactor bag, can be formed as described in detail above. Furthermore, the characteristics and advantages of the bioreactor bag and the harvesting device described above also apply for the respective features of the system.

Preferably, each of the fixing portions comprises a thickened portion.

The bioreactor bag can have fixing portions adjacent to two opposite sides, e.g., along the longitudinal axis of the bioreactor bag. A first fixing portion can be formed adjacent to the first side of the bioreactor bag and a second fixing portion can be formed adjacent to the second side of the bioreactor bag. Each of the fixing portions is preferably formed as a thickened portion. The thickened portion may comprise an elongated rod. Thus, the first thickened portion may comprise a first rod and the second thickened portion may comprise a second rod. The rods may be longish and may extend between two opposite sides substantially transverse to the longitudinal axis of the bioreactor bag, preferably in an angle of 90° across the longitudinal axis of the bioreactor bag, so that the first and second rods are parallel with each other. The advantage of such a formation of the fixing portions of the bioreactor bag is that the bioreactor bag can be easily fixed with the harvesting device in a secure manner in that the fixing portions can be fixed with the fixing devices of the harvesting device, e.g., by sliding along the thickened portions wherein the thickened portions also contributes to holding the bioreactor bag in place.

According to the present invention, a method for harvesting a content of a bioreactor bag is provided, the bioreactor bag having fixing portions at both longitudinal ends thereof and a harvesting port for draining the content of the bioreactor bag provided between said longitudinal ends, wherein the method comprises the steps of:
 fixing one of the fixing portions to a harvesting device by a first fixing device,
 fixing the other of the fixing portions to the harvesting device by a second fixing device,
 coupling the first fixing device and/or the second fixing device to the base by an adjusting device,
 selectively allowing a changing of an arrangement of the first fixing portion and/or the second fixing portion relative to the base or fixing the arrangement of the first fixing portion and/or the second fixing portion relative to the base by the adjusting device, and
 arranging and fixing the bioreactor bag in a harvesting arrangement so that the bioreactor bag hangs between the first fixing device and the second fixing device with the harvesting port being positioned substantially at the lowermost point of the bioreactor bag.

The method according to the invention performs several steps for the harvesting of a content of a bioreactor bag by means of a harvesting device, wherein the bioreactor bag and the harvesting device have all the characteristics and advantages according to the invention which have been described in detail above.

Figure 2:
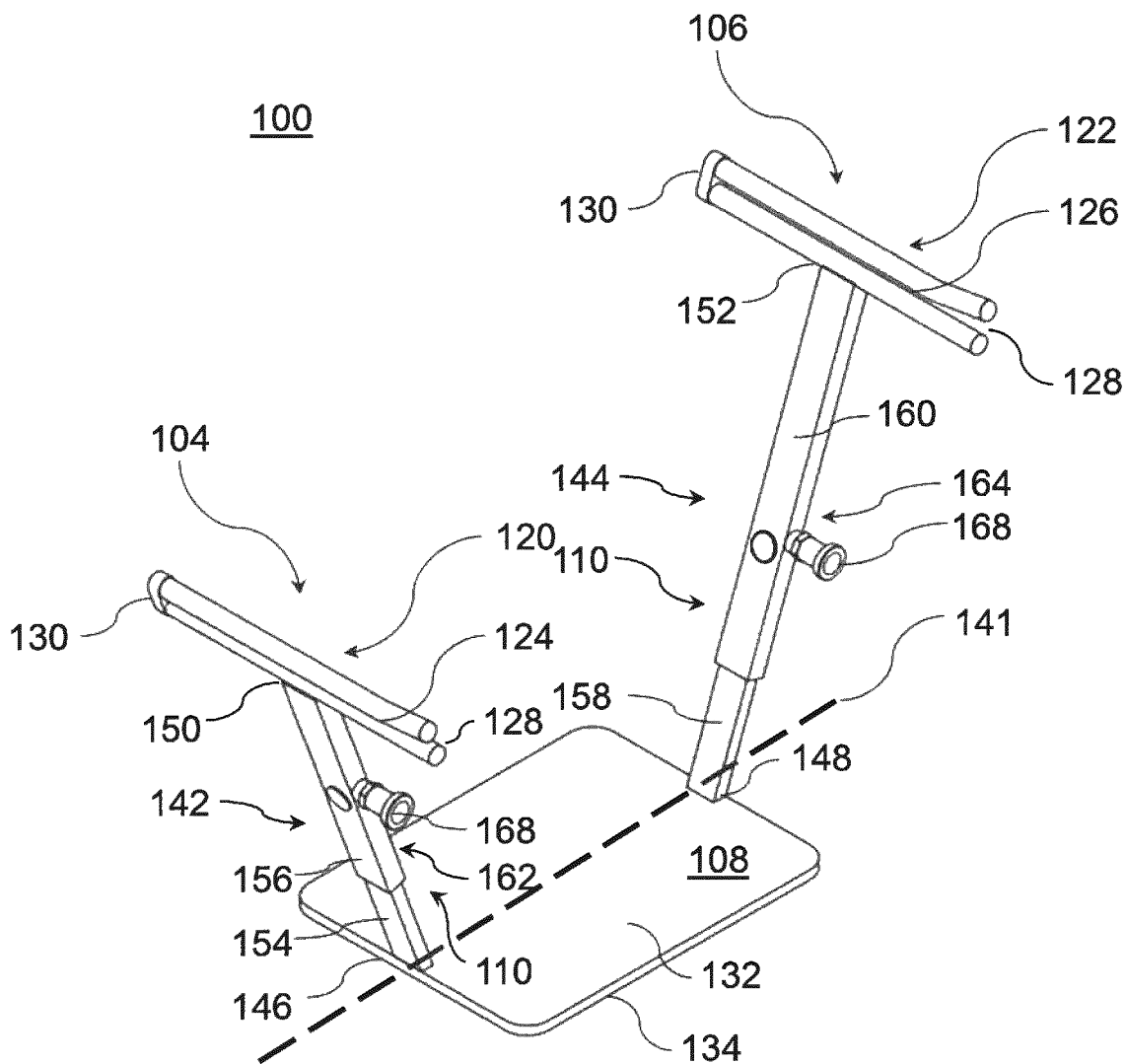
Figure 3:
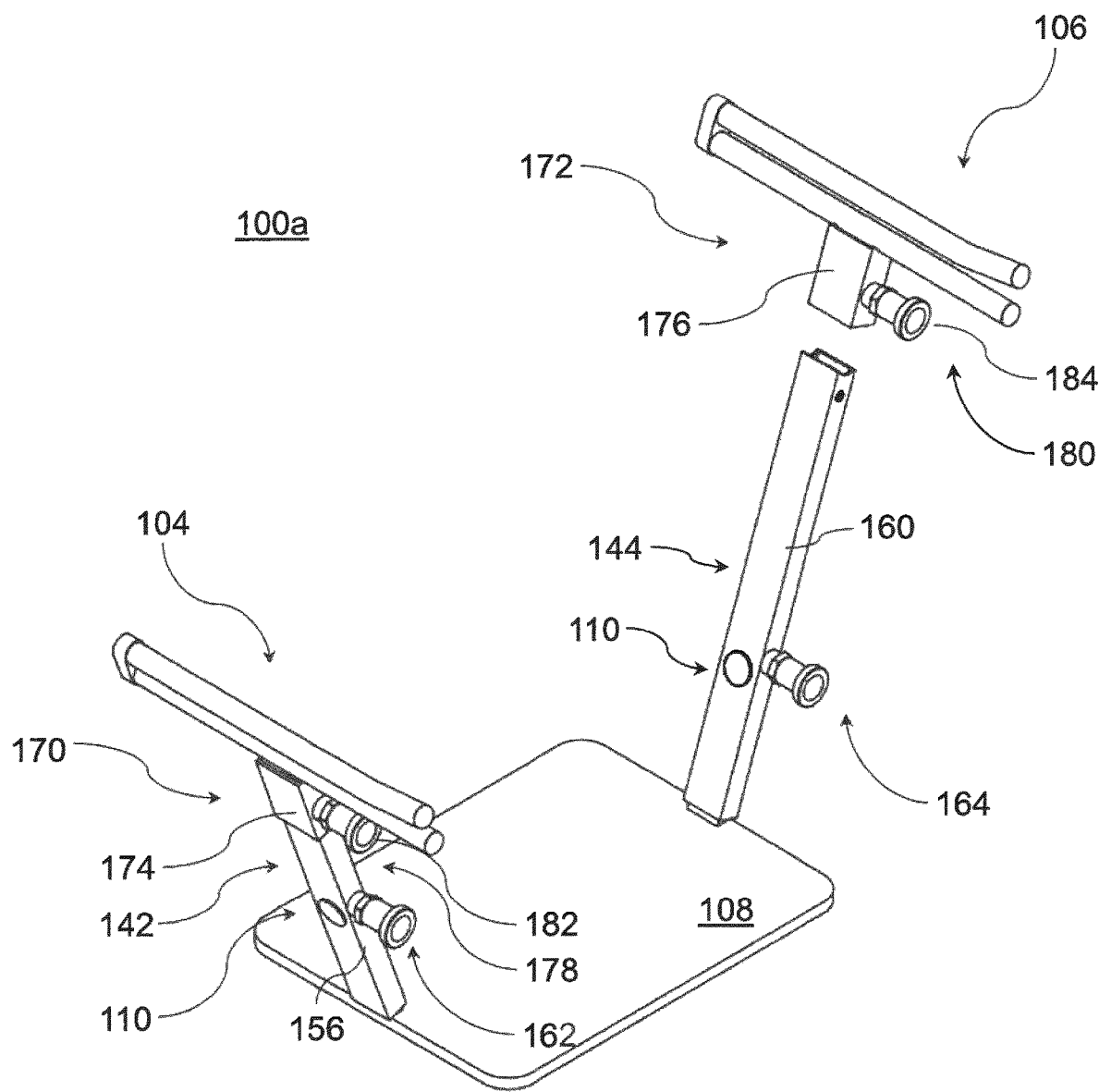
Figure 4:
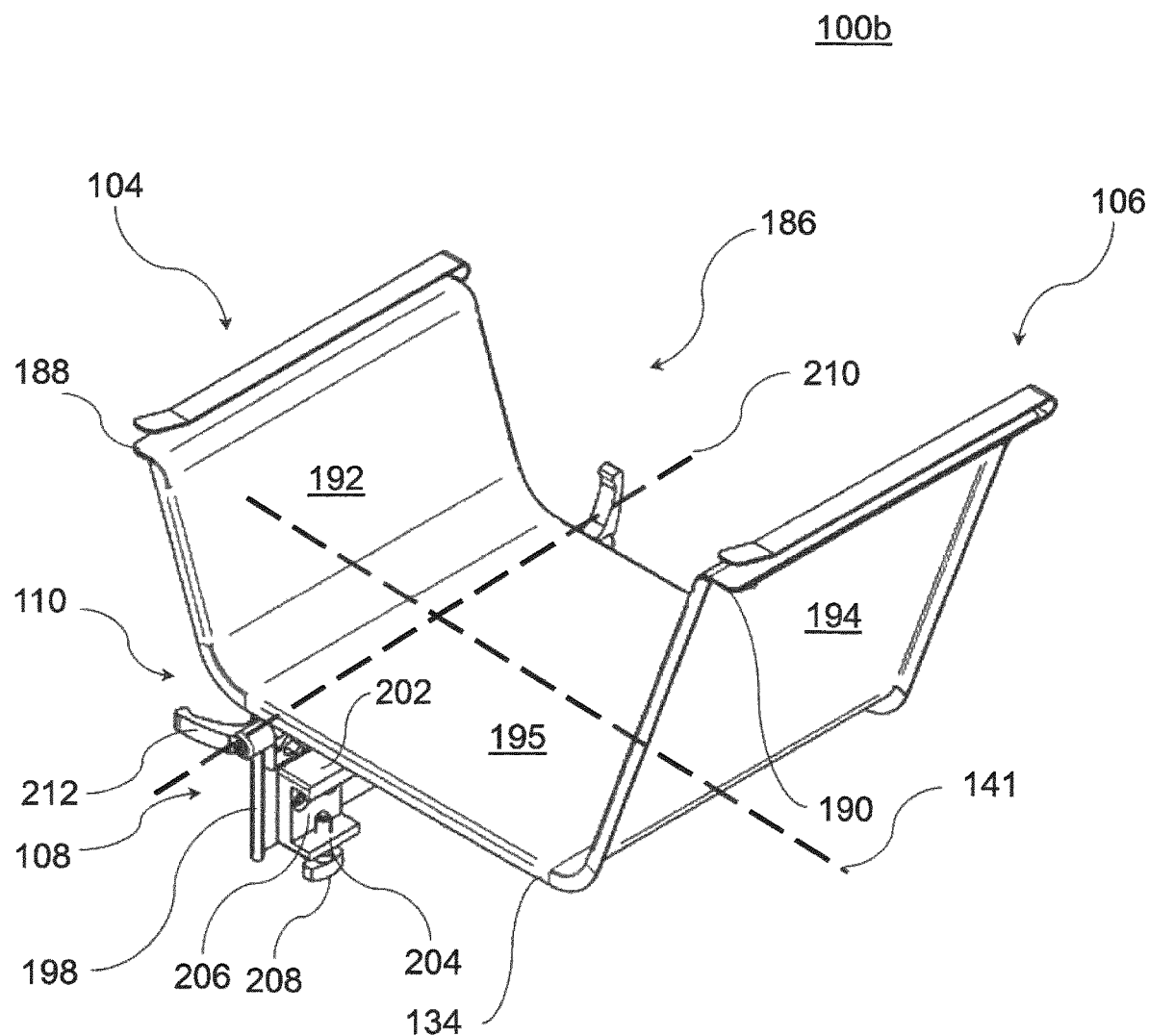
Figure 5:
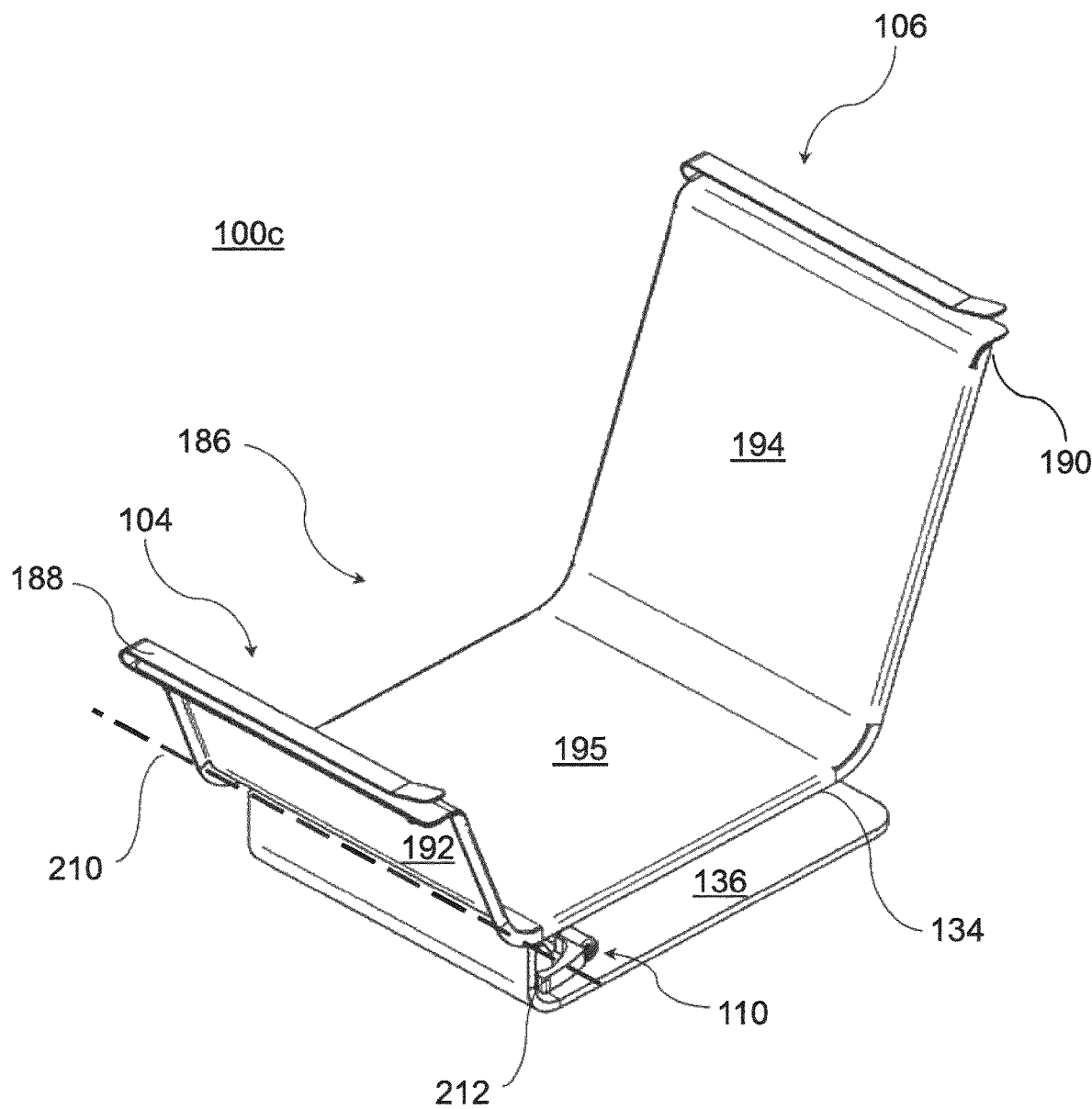
Figure 6:
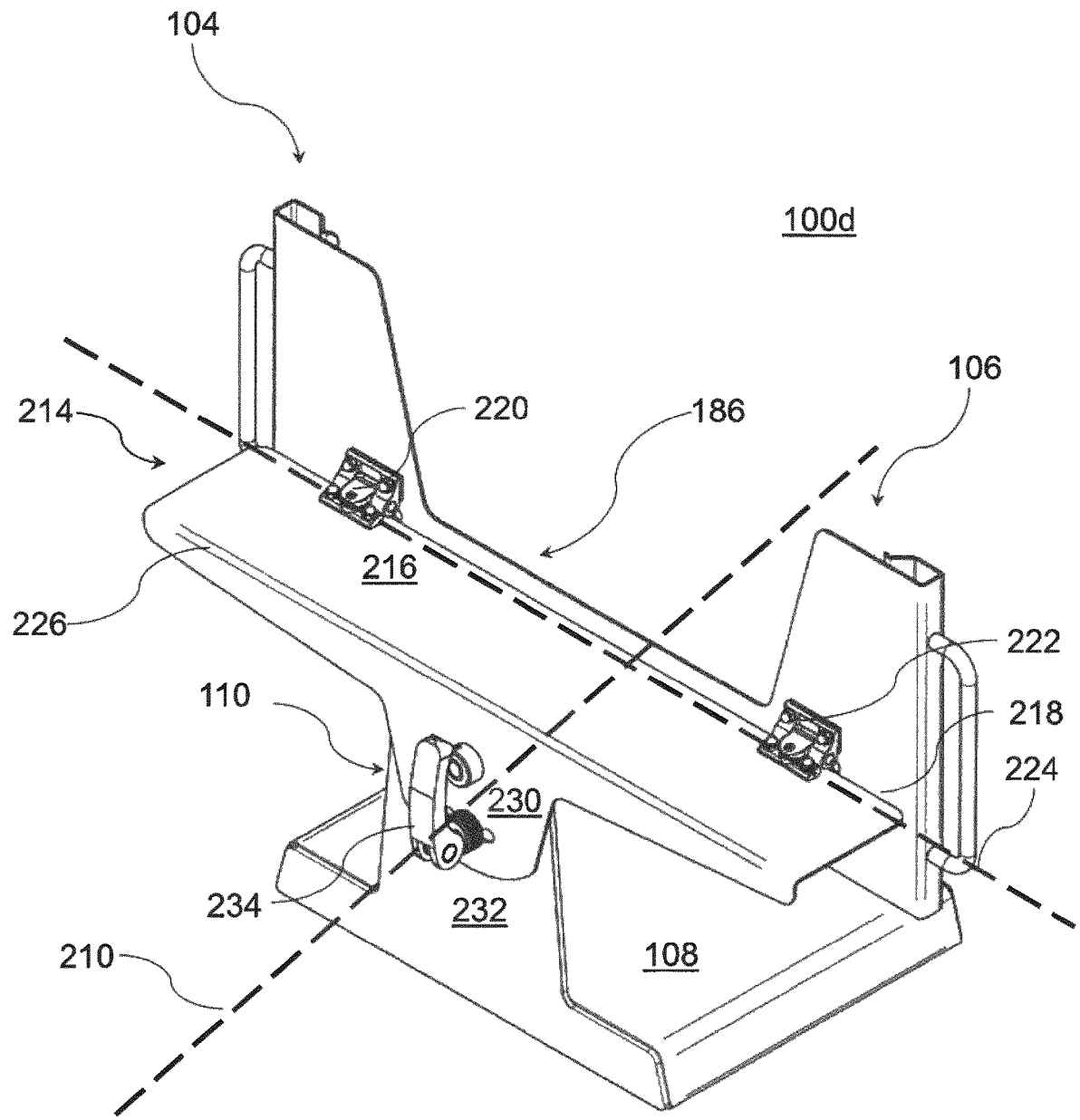
Figure 7:
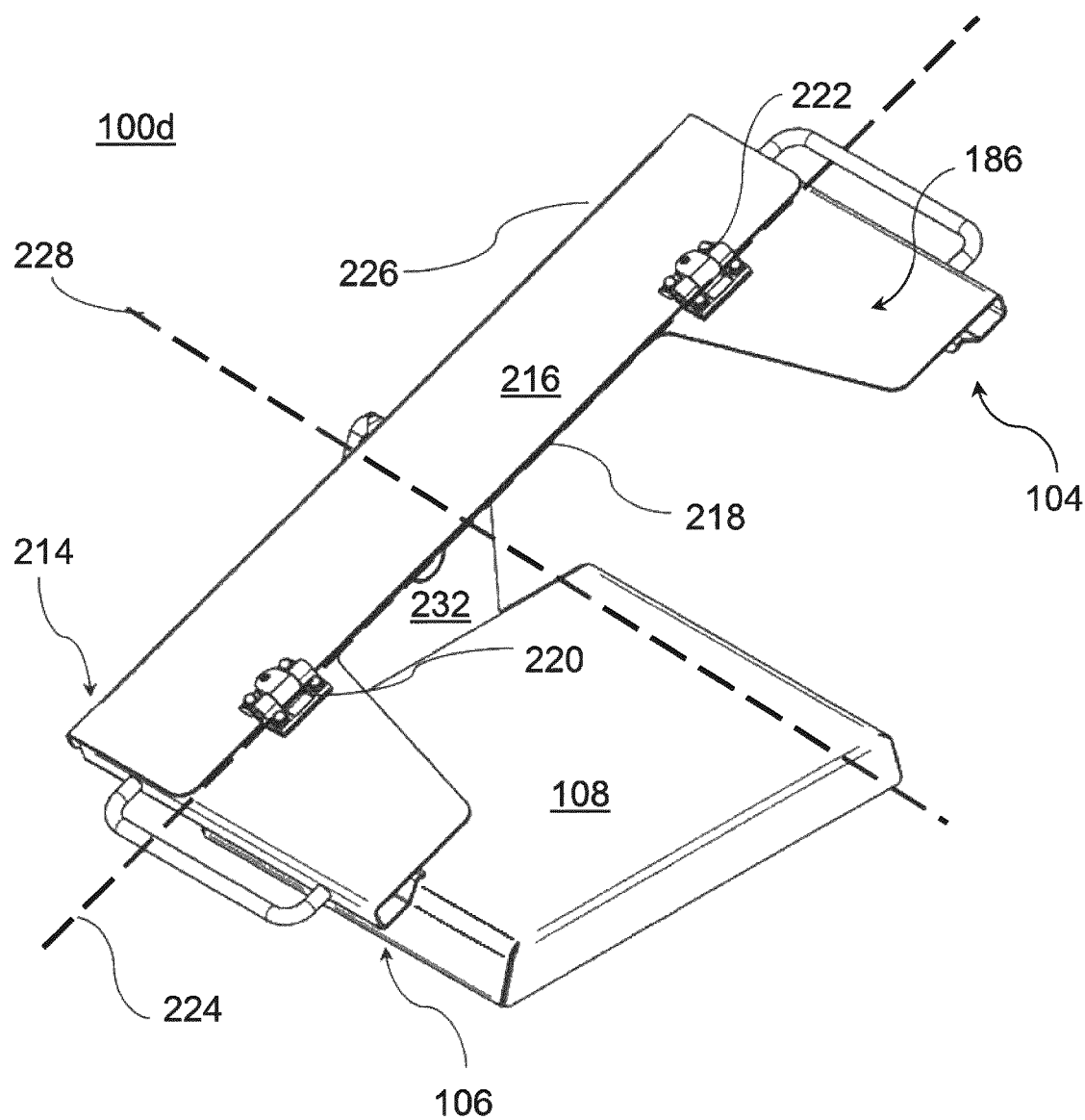
Figure 8:
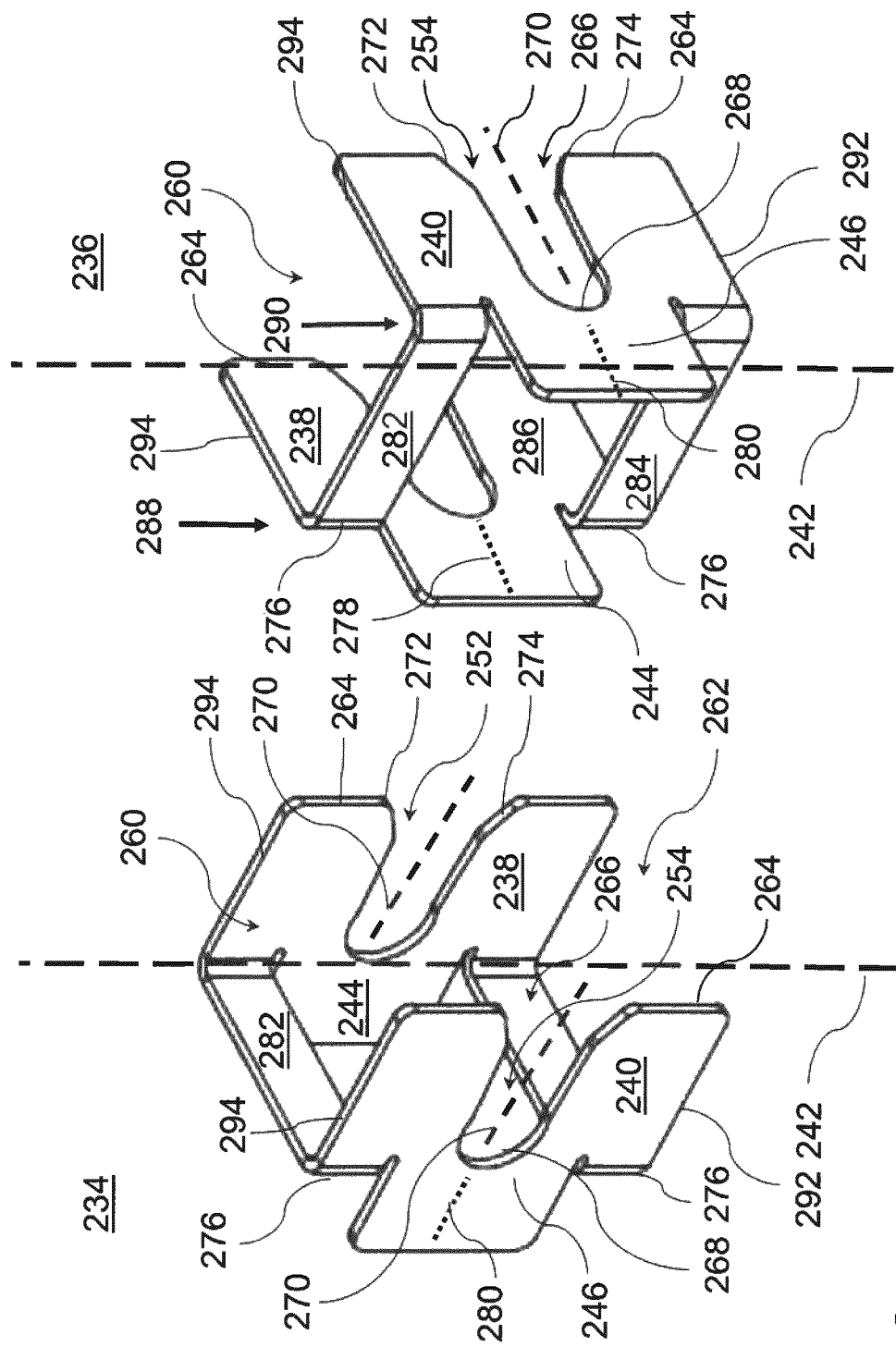
Figures 9A, 9B:
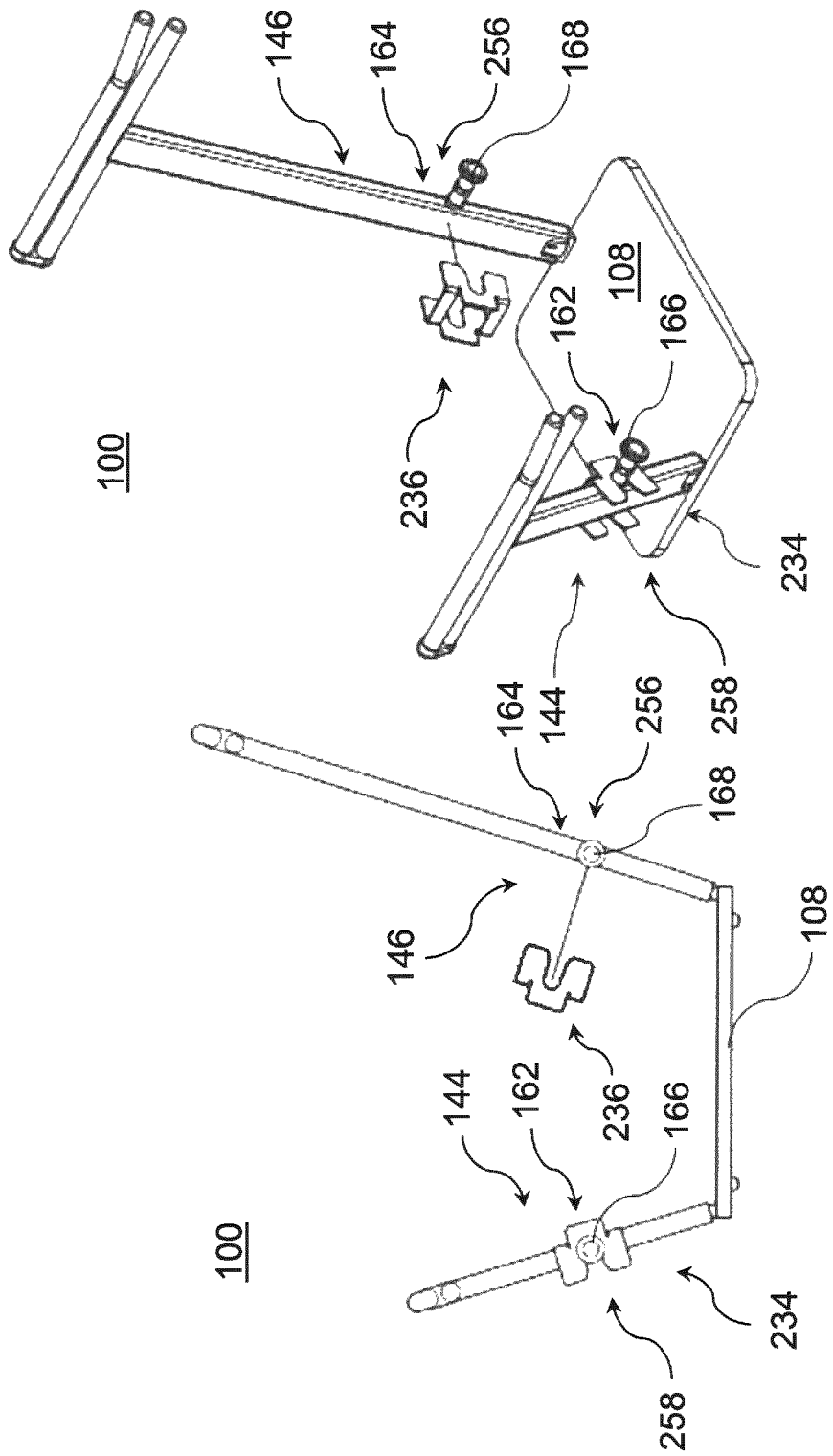
Figures 10A, 10B:
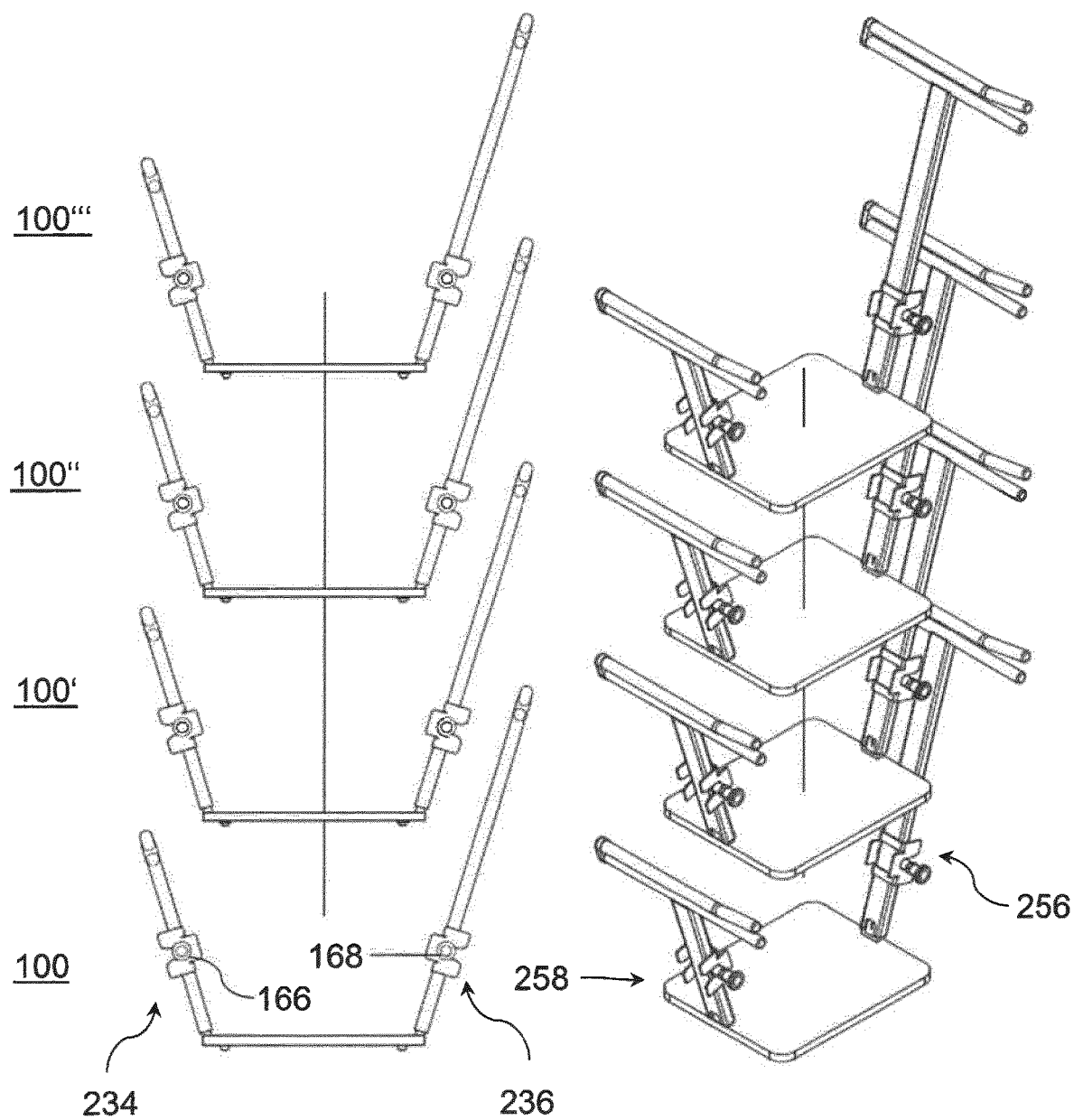

In the following the present invention will be explained on the basis of preferred embodiments shown in the drawing, in which FIG. 1 shows a side view of a first embodiment of a harvesting device according to the present invention, wherein a bioreactor bag is fixed at the fixing devices of the harvesting device, FIG. 2 shows a perspective view of the harvesting device of FIG. 1 without a bioreactor bag, FIG. 3 shows a perspective view of a second embodiment of a harvesting device according to the present invention without a bioreactor bag fixed at the fixing devices of the harvesting device, FIG. 4 shows a perspective view of a third embodiment of a harvesting device according to the present invention without a bioreactor bag fixed at the fixing devices of the harvesting device, FIG. 5 shows a perspective view of a fourth embodiment of a harvesting device according to the present invention without a bioreactor bag fixed at the fixing devices of the harvesting device, FIG. 6 shows a perspective view of a fifth embodiment of a harvesting device according to the present invention without a bioreactor bag fixed at the fixing devices of the harvesting device, wherein the fixing devices are in a fixing arrangement, FIG. 7 shows a perspective view of the harvesting device of FIG. 6, wherein the fixing devices are in a harvesting arrangement, FIG. 8 shows perspective views of an embodiment of a stacking aid, FIG. 9A shows a side view of the first embodiment of the harvesting device according to the present invention comprising two stacking aids as shown in FIG. 8, FIG. 9B shows a perspective view of the first embodiment of the harvesting device according to the present invention comprising two stacking aids as shown in FIG. 8, FIG. 10A shows a side view of four harvesting devices according to the first embodiment of the harvesting device, which are considered to be arranged and stacked with each other by means of stacking aids as shown in FIG. 8, FIG. 10B shows a perspective view of the four harvesting devices of FIG. 10A, FIG. 11A shows a side view of the four harvesting devices of FIG. 10A, which are arranged and stacked in a stacking arrangement, FIG. 11B shows a perspective view of the four harvesting devices of FIG. 10A, which are arranged and stacked in a stacking arrangement, and FIG. 11C shows an enlarged view of the encircled area in FIG. 11B showing the stacking arrangement of the harvesting devices.

FIGS. 1 and 2 show a first embodiment of a harvesting device 100 for harvesting a content of a bioreactor bag 102. The harvesting device 100 comprises a first fixing device 104, a second fixing device 106, a base 108, and an adjusting device 110. The harvesting device 100 is free of any moving device for moving the bioreactor bag 102 and/or any tempering device for tempering the bioreactor bag 102.

The bioreactor bag 102 has fixing portions 112, 114 at both longitudinal ends thereof and a harvesting port 115 for draining the content of the bioreactor bag 102 provided between said longitudinal ends on a center axis of the bioreactor bag 102 in the width direction. Adjacent to two opposite sides of the longitudinal axis of the bioreactor bag 102, the bioreactor bag 102 has a first fixing portion 112 and a second fixing portion 114. The first fixing portion 112 comprises a first thickened portion 116 and the second fixing portion 114 comprises a second thickened portion 118. The thickened portions 116, 118 comprise elongated rods welded into the bioreactor bag 102, i.e., the first thickened portion 112 comprises a first rod and the second thickened portion 114 comprises a second rod. The rods are longish and extend between two opposite sides of the bioreactor bag 102 in the width direction substantially transverse to the longitudinal axis of the bioreactor bag 102, preferably in an angle of 90° with respect to the longitudinal axis of the bioreactor bag 102, so that the first and second rods are parallel to each other.

The first fixing device 104 is formed for fixing one of the fixing portions 112, 114 of the bioreactor bag 102 to the harvesting device 100 and the second fixing device 106 is formed for fixing the other of the fixing portions 112, 114 of the bioreactor bag 102 to the harvesting device 100. The first fixing device 104 comprises a clamp 120 configured to clamp one of the fixing portions 112, 114 substantially along the width thereof. The second fixing device 106 comprises a clamp 122 configured to clamp the other of the fixing portions 112, 114 substantially along the width thereof.

Each of the clamps 120, 122 of the fixing devices 104, 106 comprises an interior space 124, 126 between two rods of the respective clamp 120, 122 extending substantially along the width of the respective fixing device 104, 106. The first fixing device 104 comprises a first space 124 and the second fixing device 106 comprises a second space 126. Each of the spaces 124, 126 extend in a plane that is substantially parallel to the base 108 and/or the horizontal plane, wherein the first space 124 extends in a different plane than the second space 126. The first fixing portion 112 of the bioreactor bag 102 can be introduced into the first space 124 and the second fixing portion 114 of the bioreactor bag 102 can be introduced into the second space 126 so that the first and second thickened portions 116, 118 are clamped between the rods of the respective clamp 120, 122 in the first and second space 124, 126. The first and second spaces 124, 126 may extend between an open end 128 of the clamps 120, 122 and a closed end 130 of the clamps 120, 122. Thus, the fixing portions 112, 114 can be easily introduced into the clamps 120, 122 via the open end 128 and may not slip out of the spaces 124, 126 at the closed end 130.

The base 108 is formed as a plate, preferably as a bed plate, having an upper surface 132 that extends across a horizontal plane. The base 108 comprises a lower surface 134 on the opposite side of the upper surface 132. The base 108 further comprises a stand 136 for placing the harvesting device 100 on a substantially horizontal surface. The stand 136 is connected to the lower surface 134 of the base 108 and comprises two support members 138, 140. The support members 138, 140 extend away from the lower surface 134 of the base 108 with an angle of 90° and have the same dimensions in the vertical and horizontal direction. The support members 138, 140 are placed on opposing peripheral regions along a longitudinal axis 141 of the base 108 and allow the harvesting device 100 to be placed on a carrier, e.g., a table or a lab bench, in a sufficiently stable manner so that the position of the harvesting port 115 at the lowermost point of the bioreactor bag 102 can be easily achieved.

The adjusting device 110 couples the first fixing device 104 and the second fixing device 106 to the base 108. The adjusting device 110 shown in FIGS. 1 to 2 comprises a first holding arm 142 and a second holding arm 144. One end of the first and second holding arms 142, 144 is connected to the base 108 and the other end of the first and second holding arms 142, 144 is connected to the first fixing device 104 and the second fixing device 106. Each of the first and second holding arms 142, 144 is configured such that the length thereof can be adjusted.

The first holding arm 142 and the second holding arm 144 are arranged on the upper surface 132 of the base 108. The first and the second holding arms 142, 144 can be integrally formed with the base 108 or can be connected with the base 108, so that first ends 146, 148 of the first and the second holding arms 142, 144 are connected with the base 108 and opposing second ends 150, 152 of the first and the second holding arms 142, 144 extend away as free ends distant from the base 108.

The holding arms 142, 144 are formed as two-piece elements so that the first holding arm 142 comprises a first rod element 154 and a second rod element 156 and the second holding arm 144 comprises a first rod element 158 and a second rod element 160. The first rod elements 154, 158 and second rod elements 156, 160 are formed as elongated rod elements having a cross-section with respect to their respective longitudinal axes with a rectangular shape. Preferably, the first rod element 154 of the first holding arm 142 and the first rod element 158 of the second holding arm 144 have a cross-section with respect to its longitudinal axis with an outer diameter that is smaller than the inner diameter of the cross-section of the second rod element 156 of the first holding arm 142 and the second rod element 160 of the second holding arm 144, respectively. Furthermore, the second rod elements 156, 160 are each formed with an inner cavity so that the first rod elements 154, 158 can be inserted into the second rod elements 156, 160, respectively.

A first end of the first rod elements 154, 156 of the first and second holding arms 142, 144 is connected to the base 108 of the harvesting device 100, preferably the upper surface 132 of the base 108, and an opposing, second end of the first rod elements 154, 156 is introduced into a first end of the second rod elements 156, 160 of the first and the second holding arms 142, 144, respectively. A second end of the second rod element 156 of the first holding arm 142 opposing to the first end of the second rod element 156 is connected with the first fixing device 104. A second end of the second rod element 160 of the second holding arm 144 opposing to the first end of the second rod element 160 is connected to the second fixing device 106. Based on this configuration of the first and the second holding arms 142, 144 the distance of the first fixing device 104 and of the second fixing device 106 is adjustable with respect to the base 108 of the harvesting device 100. Thus, the distance of the first fixing device 104 to the base 108 is adjustable in order to be equal to the distance of the second fixing device 106 to the base 108 or in order to be larger or smaller than the distance of the second fixing device 106 to the base 108.

The first holding arm 142 is positioned at a peripheral region of the upper surface 132 of the base 108 and the second holding arm 144 is positioned at another peripheral region of the upper surface 132 that is distinct from the first peripheral region. In particular, the holding arms 142, 144 are positioned at opposing peripheral regions along the longitudinal axis 141 of the base 108.

The first holding arm 142 comprises a first lock 162 and the second holding arm 144 comprises a second lock 164 in order to fix the first rod elements 154, 158 and the second rod elements 156, 160 of each of the holding arms 142, 144 to each other. The first lock 162 comprises a first bolt 166 that penetrates a through-hole within the second rod element 156 of the first holding arm 142 in order to engage with the first rod element 154 of the first holding arm 142 so that the distance between the first fixing device 104 and the base 108 can be adjusted. The second lock 164 comprises a second bolt 168 that penetrates a through-hole within the second rod element 160 of the second holding arm 144 in order to engage with the first rod element 158 of the second holding arm 144 so that the distance between the second fixing device 106 and the base 108 can be adjusted. Thus, the harvesting device 100 is configured such that the bioreactor bag 102 can be arranged and fixed in a harvesting arrangement in which the bioreactor bag 102 hangs between the first fixing device 104 and the second fixing device 106 with the harvesting port 115 being positioned substantially at the lowermost point of the bioreactor bag 102, as shown in FIG. 1. The adjusting device 110 is configured to selectively allow changing an arrangement of the first fixing portion 112 and/or the second fixing portion 114 relative to the base 108 or fixing the arrangement of the first fixing portion 112 and/or the second fixing portion 114 relative to the base 108. In particular, the first fixing portion 112 of the bioreactor bag 102 can be fixed with the first fixing device 104 of the harvesting device 100 in that the first fixing portion 112 of the bioreactor bag 108 is introduced into the first space 124 of the first fixing device 104 that is formed by the first clamp 120. The second fixing portion 114 of the bioreactor bag 108 can be fixed with the second fixing device 106 of the harvesting device 100 in that the second fixing portion 114 of the bioreactor bag 102 is introduced into the second space 126 of the first fixing device 104 that is formed by the second clamp 122. Afterwards, the distance of the first and second fixing devices 104, 106 relative to the base 108 is adjusted by means of the adjusting device 110. In particular, the distance of the first fixing device 104 to the base 108 is adjusted in that the second rod element 156 is moved over the first rod element 154 and thus toward the base 108 until the desired position or the desired distance between the first fixing device 104 and the base 108, is achieved. The desired position or the desired distance is locked by the first lock 162 of the adjusting device 110. The distance of the second fixing device 106 to the base 108 is adjusted in that the second rod element 160 is moved over the first rod element 158 toward the base 108 until the desired position or the desired distance between the second fixing device 106 and the base 108, is achieved. The desired position or the desired distance is locked by the second lock 164 of the adjusting device 110. This allows an optimized adjustment of the fixing portions 112, 114 of the bioreactor bag 102 which have been introduced into the fixing devices 104, 106 so that the harvesting port 115 of the bioreactor bag 102 agrees with the lowermost point of the bioreactor bag 102. An optimized harvesting, draining or transfer of the content of the bioreactor bag 102 by means of gravity is consequently enabled.

FIG. 3 shows a second embodiment of a harvesting device 100a for harvesting a content of a bioreactor bag 102. The second embodiment of a harvesting device 100a distinguishes from the first embodiment of a harvesting device 100 in that the first and second fixing devices 104, 106 are detachably attached to the first and second holding arms 142, 144 by means of a first and second attachment device 170, 172, respectively.

The first attachment device 170 comprises a rod element 174 that is attached to the first fixing device 104 with one of its opposing ends. The second attachment device 172 comprises a rod element 176 that is attached to the second fixing device 106 with one of its opposing ends. The rod elements 174, 176 have a cross section transverse to their respective longitudinal axis that is larger than the cross section of the second rod elements 156, 160 of the holding arms 142, 144 of the adjusting device 110, respectively. The rod elements 174, 176 have an inner cavity, so that they can be moved with one end opposing to the end that is attached to the first and second fixing devices 104, 106 over the second rod elements 156, 160 of the holding arms 142, 144, respectively, toward the base 108. The first and second attachment devices 170, 172 further comprise third and fourth locks 178, 180 so that they can be locked with the second rod elements 156, 160, respectively. The third and fourth locks 178, 180 are similarly formed as the first and second locks 162, 164 of the holding arms 142, 144, i.e., each lock 178, 180 comprises a bolt 182, 184 that penetrates a second through-hole within the outer walls of the rod elements 174, 208 in order to engage with the second rod elements 156, 160, respectively, so that the first and second attachment devices 170, 172 are fixed to the second rod elements 156, 160, respectively.

By means of the first and second attachment devices 170, 172, the fixing portions 112, 114 of the bioreactor bag 102 can be first fixed with the fixing devices 104, 106 in the above described manner. Afterwards, the bioreactor bag 102 can be fixed to the harvesting device 100a in that the first and second attachment devices 170, 172 are attached to the second rod elements 156, 160 of the holding arms 142, 144 of the adjusting device 110, respectively. This allows a convenient and user-friendly attachment of the bioreactor bag 102 to the harvesting device 100a.

FIG. 4 shows a third embodiment of a harvesting device 100b for harvesting a content of a bioreactor bag 102. The third embodiment of a harvesting device 100b distinguishes from the first and second embodiments of a harvesting device 100, 100a in that the first and second fixing devices 104, 106 are fixedly connected to each other via a connecting structure 186, and in that the base 108 comprises an attaching mechanism 198.

In particular, the first and second fixing devices 104, 106 are connected to each other by a connecting structure 186, wherein the connecting structure 186 is connected to the adjusting device 110. The connecting structure 186 is formed by a sheet that is arcuated in a concave manner. The connecting structure 186 is coupled to the base 108 via the adjusting device 110. The connecting structure 186 comprises a bridging portion 195, a first and a second free end 188, 190 extending away from the bridging portion 195, wherein the first and second fixing devices 104, 106 are integrally formed with the first and second free ends 188, 190, respectively. The connecting structure 186 comprises a first and a second uprising portion 192, 194, wherein the first and second uprising portions 192, 194 extend away from peripheral regions of the bridging portion 195 which are opposing each other along the longitudinal axis 141 of the connecting structure 186. The length of the first uprising-portion 192 may be equal to or different to the length of the second uprising portion 194 with respect to the bridging portion 195 of the harvesting device 100b. In other words, the distance between the first free end 188 of the connecting structure 186 to the bridging portion 195 can be equal to or different to the distance between the second free end 190 of the connecting structure 186 to the bridging portion 195. In the third embodiment shown in FIG. 4, the distance between the first free end 188 to the bridging portion 195 is shorter than the distance between the second free end 190 to the bridging portion 195.

The connecting structure 186 has a substantially concave shape in cross section, wherein the concave shape opens upward in the harvesting arrangement. The concave shape has a symmetrical cross section across the longitudinal axis of the harvesting device 100b. The location of the first and second fixing devices 104, 106 is at the free ends of the two uprising portions 192, 194.

The bridging portion 195 is attached to the attaching mechanism 198 for attaching the harvesting device 100b to a frame structure. The attaching mechanism 198 comprises a hinge joint for tilting the connecting structure 186 about the tilt axis 210 with respect to the base 108, wherein the attaching mechanism 198 is connected to a lower surface of the bridging portion 195. The tilt axis 210 extends in parallel to the fixing devices 104, 106 of the harvesting device 100b. The frame structure can be any conventional frame structure such as a guide rail that is attached to a carrier, e.g., a table or a lab bench. However, it is also possible to attach the harvesting device 100b via the attaching mechanism 198 directly to a table or a lab bench, e.g., to an edge portion of a table plate or a lab bench plate. The attaching mechanism 198 comprises two parallel protrusions 202, 204 extending away from an attachment base 206, wherein one of the two protrusions 202, 204 comprises a through hole with a bolt 208 extending therethrough. Thus, the harvesting device can be attached via the attachment mechanism 198 to the frame, the table or the lab bench in that an element of the frame, the table or the lab bench is placed between the two protrusions 202, 204, and the bolt 206 extending through the through hole is manually tightened to engage with the respective element of the frame, table or lab bench.

The adjusting device 110 comprises a tilting mechanism for tilting the first fixing device 104 and the second fixing device 106 with respect to the base 108. The tilting mechanism comprises only one rotary degree of freedom about the tilt axis 210. The adjusting device 110 is configured so that the connecting structure 186 and the first and second fixing devices 104, 106 fixed thereto are tilted. The tilt axis 210 extends substantially parallel to the spaces 124, 126 which are formed within each of the fixing devices 104, 106. Thus, after the bioreactor bag 102 has been fixed with the fixing portions 104, 106 of the harvesting device 100b, the harvesting device 100b can be tilted about the tilt axis 210 by means of the tilting mechanism of the adjusting device 110.

The adjusting device 110 shown in FIG. 4 comprises a lock 212 in order to fix the tilted harvesting device 100b at a preferred position about the tilt axis 210. This lock 212 comprises a lever element which can be manually turned so as to tighten a bolt and to fix the connecting structure 186 with respect to the base 108 by means of friction. This allows a convenient adjustment of the preferred position of the harvesting device 100b and the fixing of the harvesting device 100b after having achieved the desired tilted position.

Thus, the harvesting device 100b is configured such that the bioreactor bag 102 can be arranged and fixed in a harvesting arrangement in which the bioreactor bag 102 hangs within the connecting structure 186 between the first fixing device 104 and the second fixing device 106 with the harvesting port 115 being positioned substantially at the lowermost point of the bioreactor bag 102. By means of the attaching mechanism 198, the harvesting device 100b is attachable to any desired location of a frame structure so that a user can mount the bioreactor bag 102 to the harvesting device 100b in a convenient manner, e.g., while standing or sitting. It also enables efficient use of lab space.

The adjusting device 100b is configured to selectively allow changing an arrangement of the first fixing portion 112 and/or the second fixing portion 114 relative to the base 108 or fixing the arrangement of the first fixing portion 112 and/or the second fixing portion 114 relative to the base 108. In particular, the harvesting device 100b comprising the first and second fixing devices 104, 106 can be tilted about the tilt axis 210 so that the position of the first and second fixing devices 104, 106 about the tilt axis 210 with respect to the base 108 is changed. The desired position is locked by means of the lock 212. This allows an optimized adjustment of the fixing portions 112, 114 of the bioreactor bag 102 that has been introduced into the fixing devices 104, 106 so that the harvesting port 115 of the bioreactor bag 102 agrees with the lowermost point 115 of the bioreactor bag 102. An optimized harvesting, draining or transfer of the content of the bioreactor bag 102 by means of gravity is consequently enabled.

FIG. 5 shows a fourth embodiment of a harvesting device 100c for harvesting a content of a bioreactor bag 102. The fourth embodiment of a harvesting device 100c distinguishes from the third embodiment of a harvesting device 100b in that the base 108 comprises a stand 136 for placing the harvesting device 100c on a substantially horizontal surface. The stand 136 is integrally formed with a main body of the base 108 and is formed as a plate that extends in a horizontal plane.

Thus, the harvesting device 100c can be placed on the ground or on a carrier, e.g., a table or a lab bench, in a sufficiently stable manner so that the position of the harvesting port 115 at the lowermost point of the bioreactor bag 102 can be easily achieved.

FIGS. 6 and 7 show a fifth embodiment of a harvesting device 100d for harvesting a content of a bioreactor bag 102. The fifth embodiment of a harvesting device 100d distinguishes from each of the preceding embodiments of a harvesting device 100, 200, 300, 400 in that the first and second fixing devices 104, 106 are connected to each other by a connecting structure 186, wherein the first and second fixing devices 104, 106 are pivotable between a fixing arrangement (FIG. 6) and the harvesting arrangement (FIG. 7).

In particular, the connecting structure 186 comprises a pivoting mechanism 214 allowing the first and second fixing devices 104, 106 to be pivotable between the harvesting arrangement and the fixing arrangement for fixing the bioreactor bag 102 to the harvesting device 100d, independently from the adjusting device 110. The connecting structure 186 is connected to the adjusting device 110 via the pivoting mechanism 214. The pivoting device 214 comprises a substantially planar portion 216, which has an upper surface. A first end portion 218 transverse to the longitudinal axis of the pivoting element 216 is connected via pivoting means 220, 222, e.g. first and second hinges, with the portion of the connecting structure 186 connecting the first and second fixing devices 104, 106, so that the connecting structure 186 is pivotable about a pivot axis 224. The pivot axis 224 extends substantially in the plane of the substantially planar portion 216.

In the fixing arrangement, the connecting structure 186 is in a first position, wherein the first and second fixing devices 104, 106 extend in a plane that is transverse to the plane of the substantially planar portion 216 or to the horizontal plane, preferably at an angle of about 90°. The first position of the connecting structure 186 allows a convenient fixing of the bioreactor bag 102 with the first and second fixing devices 104, 106 so that the fixing portions 112, 114 of the bioreactor bag 102 can be easily introduced into the fixing devices 104, 106.

The connecting structure 186 can be pivoted about the pivot axis 224 from the first position into a second position so that the first and second fixing devices 104, 106 are pivoted into the harvesting arrangement. In the second position, the first and second fixing devices 104, 106 extend in a plane that is parallel to the plane of the substantially planar portion 216 or to the horizontal plane, preferably at an angle of about 0°. The second position of the connecting structure 186 allows the bioreactor bag 102 to hang between the first fixing device 104 and the second fixing device 106 with the harvesting port 115 being positioned substantially at the lowermost point of the bioreactor bag 102.

A second end portion 226 opposing to the first end portion 218 of the upper surface of the pivoting element 216 is connected to the adjusting device 110 so that the connecting structure 186 is pivotable about the tilt axis 210. The tilt axis 210 extends substantially transverse to the pivot axis 224, preferably at an angle of about 90°. The tilt axis 210 extends in a plane that is parallel to the plane of the substantially planar portion 216 or to the horizontal plane.

The pivoting mechanism 214 comprises a first projecting element 230 and the adjusting device 110 comprises a second projecting element 232. The first projecting element 230 is formed as a flat side element protruding downward from the second end portion 226 of the substantially planar portion 216. The second projecting element 232 is formed as a flat side element connected in a fixed manner with one of the end portions of the base 108 and protrudes upward and away from the base 108. The two projecting elements 230, 232 are connected to each other in such a manner that the first projecting element 230 lies against the second protruding element 232 so that the first projecting element 230 can be pivoted about the tilt axis 210 while sliding along the second projecting element 232.

The adjusting device 110 comprises a lock 212 in order to fix the tilted harvesting device 100d and thus the first and second fixing devices 104, 106 at a preferred position around the tilt axis 210. This lock 212 comprises a lever element and a bolt that extends at least through the first projecting element 230 of the pivoting mechanism 214.

Thus, after the fixing of the fixing portions 112, 114 of the bioreactor bag 102 with the fixing devices 104, 106 of the harvesting device 100d in the fixing arrangement, the connecting structure 186 is pivoted about the pivot axis 224 from the first position into the second position in the harvesting arrangement so that the bioreactor bag 102 hangs between the first fixing device 104 and the second fixing device 106. In the harvesting arrangement, the connecting structure 186 is tilted about the tilt axis 210 so that the harvesting port 115 of the bioreactor bag 102 is positioned substantially at the lowermost point of the bioreactor bag 102.

FIGS. 8 to 11C shows stacking aids 234, 236, wherein each of the stacking aids 234, 236 is configured to be detachably mounted to a mounting portion 256, 258 of the first embodiment of a harvesting device 100 for harvesting a content of a bioreactor bag 102 such that another harvesting device 100' can be arranged and stacked in a stacking arrangement onto the harvesting device 100. The stacking aid 234, 236 is configured to prevent a lateral displacement of the harvesting devices 100, 100' relative to each other in the stacking arrangement.

FIG. 8 shows perspective views of the stacking aids 234, 236. Each of the stacking aids 234, 236 comprises a first lateral portion 238 and a second lateral portion 240, wherein the first and second lateral portions 238, 240 are arranged on opposing lateral sides of a stacking aid longitudinal axis 242. The first and second lateral portions 238, 240 comprise a first and second mounting recess 252, 254, respectively, wherein the mounting recesses 252, 254 are configured to at least partly receive the mounting portion 256, 258 of the harvesting device 100, respectively. The mounting portion 256, 258 is formed by a portion of the first holding arm 142 and/or the second holding arm 144. Preferably, the mounting portion 256, 258 is formed by the first lock 162 comprising a first bolt 166 and/or the second lock 164 comprising a second bolt 168. Opposing ends 260, 262 of the stacking aids 234, 236 in the direction of the stacking aid longitudinal axis 242 are formed open and opposing ends of the stacking aids 234, 236 in a lateral direction transverse or perpendicular to the stacking aid longitudinal axis 242 are formed by the first lateral portion 238 and the second lateral portion 240.

FIGS. 9A and 9B show that the open ends 260, 262 are arranged in the direction of the stacking aid longitudinal axis 242 and allow an easy arrangement of the harvesting devices 100, 100' one upon the other. In particular, the open ends 260, 262 allow the reception of the first holding arm 142 in the vicinity of the first lock 162 and/or the reception of the second holding arm 144 in the vicinity of the second lock 164. Thus, in the stacking arrangement, the stacking aids 234, 236 are detachably mounted to the mounting portions 256, 258, wherein the first holding arm 142 and the second holding arm 144 extend along the stacking aid longitudinal axis 242 between the opposing open ends 260, 262 and beyond the opposing open ends 260, 262, wherein the first lateral portion 238 and the second lateral portion 240 abut against opposing edges or surfaces of the first holding arm 142 or the second holding arm 144.

The first and second lateral portions 238, 240 are formed in a sheet-like manner. The entire stacking aid 234, 236 comprising the first and second lateral portions 238, 240 is formed from a sheet metal. The first lateral portion 238 comprises the first mounting recess 252 and the second lateral portion 240 comprises the second mounting recess 254. The mounting recesses 252, 254 extend from an edge 264 of the first and second lateral portions 238, 240 within the first and second lateral portions 238, 240 in a plane substantially traverse or perpendicular to the stacking aid longitudinal axis 242, respectively. Thus, the mounting recesses 252, 254 can extend between a first, open end 266 in the vicinity of the lateral edge 264 of the first and second lateral portions 238, 240 and a second, closed end 268. The mounting recesses 252, 254 extend between the first, open end 266 and the second, closed end 268 along a mounting recess longitudinal axis 270, respectively. The mounting recess longitudinal axis 270 extends in a plane which is substantially transverse or perpendicular to the plane of the stacking aid longitudinal axis 242.

The second, closed end 268 is semi-circularly formed in the plane of the first or second lateral portion 238, 240 and has a diameter which is at least as large as the diameter of the first bolt 166 of the first lock 162 and/or the second bolt 168 of the second lock 164. Thus, the stacking aids 234, 236 can be arranged around the first bolt 166 and/or around the second bolt 168 of the locks 162, 164. The first and second bolts 166, 168 can be received by the mounting recesses 252, 254. In the stacking arrangement, the first bolt 166 and the second bolt 168 abut against the second, closed end 268 of the mounting recesses 252, 254, respectively.

Each of the mounting recesses 252, 254 comprises opposing rounded edges 272, 274 in the vicinity of the first, open end 266. The opposing rounded edges 272, 274 are located on opposing sides in a direction transverse or perpendicular to the mounting recess longitudinal axis 270. The rounded edges 272, 274 allow an easy introduction of the first bolt 166 and the second bolt 168 into the mounting recesses 252, 254 and an easy reception of the first bolt 164 and the second bolt 166 in the mounting recesses 252, 254.

The first lateral portion 238 comprises a first protrusion 244 and the second lateral portion 240 comprises a second protrusion 246, wherein the first and second protrusions 244, 246 protrude substantially in a height direction perpendicular to the stacking aid longitudinal axis 242 and the stacking aid lateral direction substantially parallelly to each other. The first and second protrusions 244, 246 are configured to hold a holding portion of the harvesting device 100' in the stacking arrangement. The first and second protrusions 244, 246 extend parallelly in the same direction relative to the stacking aid longitudinal axis 242. The first and second protrusions 244, 246 protrude from an edge 276 of the lateral portions 238, 244, which is opposing to the edge 264 in the vicinity of the first, open end 266 of the mounting recesses 252, 254.

The first protrusion 244 extends along a first protrusion longitudinal axis 278 which extends in the same plane as the mounting recess longitudinal axis 270 of the first lateral portion 238, wherein the first protrusion longitudinal axis 278 and the mounting recess longitudinal axis 238 may extend substantially along a common straight line within the plane. The second protrusion 246 extends along a second protrusion longitudinal axis 280 which extends in the same plane as the mounting recess longitudinal axis 270 of the second lateral portion 240, wherein the second protrusion longitudinal axis 280 and the mounting recess longitudinal axis 270 extend substantially along a common straight line within the plane.

The stacking aids 234, 236 are formed substantially plane symmetrically with respect to a symmetry plane including the stacking aid longitudinal axis 242 and arranged perpendicular to the stacking aid lateral direction. The first lateral portion 238 and the second lateral portion 240 are arranged parallel to each other and parallel to the symmetry plane. The first and second mounting recesses 252, 254 are arranged parallel to each other and have identical shapes and/or dimensions. The first and second protrusions 244, 246 are parallel to each other and parallel to the symmetry plane.

The first and second lateral portions 238, 240 of each stacking aid 234, 236 are connected to each other by a first connecting sheet 282 and a second connecting sheet 284, which connect the first and lateral portions 238, 240 above and below the first and second protrusions 244, 246 in a direction transverse or perpendicular to the stacking aid longitudinal axis 242. The stacking aids 234, 236 comprise an opening 286 between the first connecting sheet 282 and the second connecting sheet 284, wherein the width of the opening 286 is at least twice as large as the width of each of the first and second protrusions 244, 246, respectively. The dimension of the opening 286 in the stacking aid longitudinal direction is substantially the same as the dimension of the first and second protrusions 244, 246 in the stacking aid longitudinal direction, respectively. Each of the stacking aids 234, 236 are easily formed from a sheet material, e.g., a sheet metal, wherein the mounting recesses 252, 254 are cut out from opposing sides of the sheet material and wherein the first and second protrusions 244, 246 may be cut out from an area in-between the two mounting recesses 252, 254.

FIGS. 10A to FIG. 11C show perspective views and side views of four harvesting devices 100, 100', 100", 100''', which are arranged and stacked in a stacking arrangement with respect to each other. Two stacking aids 234, 236 are detachably mounted to the first and second mounting portions 256, 258 of each of the four harvesting devices 100, 100', 100", 100''', respectively. The second harvesting device 100' is arranged and stacked onto the (first) harvesting device 100 in a stacking arrangement, the third harvesting device 100" is arranged and stacked onto the second harvesting device 100' in a stacking arrangement, and the fourth harvesting device 100′′′ is arranged and stacked onto the third harvesting device 100′′ in a stacking arrangement.

Thus, the two stacking aids 234, 236 are detachably mounted to the mounting portions 256, 258 of the first harvesting device 100, wherein the first and second bolts 166, 168 of the holdings arms 142, 144 of the first harvesting device 100 are received by the mounting recesses 252, 254 of the stacking aids 234, 236. At the same time, a form fit in the lateral direction with respect to the holding portion of the second harvesting device 100′ is established. The first and second protrusions 244, 246 of the stacking aids 234, 236 detachably mounted to the mounting portions 256, 258 of the first harvesting device 100 prevent a lateral displacement of the second harvesting device 100′. Two stacking aids 234, 236 are also detachably mounted to the mounting portions of the second harvesting device 100′, wherein the first and second bolts 166, 168 of the holdings arms 142, 144 of the second harvesting device 100′ are received by the mounting recesses 252, 254 of the stacking aids 234, 236. At the same time, a form fit in the lateral direction with respect to the holding portion of the third harvesting device 100′′ is established. The first and second protrusions 244, 246 of the stacking aids 234, 236 detachably mounted to the mounting portions 256, 258 of the second harvesting device 100′ prevent a lateral displacement of the third harvesting device 100′′. Finally, two stacking aids 234, 236 are also detachably mounted to the mounting portions of the third harvesting device 100′′, wherein the first and second bolts 166, 168 of the holdings arms 142, 144 of the third harvesting device 100′′ are received by the mounting recesses 252, 254 of the stacking aids 234, 236. At the same time, a form fit in the lateral direction with respect to the holding portion of the fourth harvesting device 100′′′ is established. The first and second protrusions 244, 246 of the stacking aids 234, 236 detachably mounted to the mounting portions 256, 258 of the third harvesting device 100′′ prevent a lateral displacement of the fourth harvesting device 100′′′.

In the stacking arrangement, lower edges 292 of the lateral portions 238, 240 of the stacking aids 234, 236 of the second harvesting device 100′ abut against upper edges 294 of the lateral portions 238, 240 of the stacking aids 234, 236 of the first harvesting device 100′. Furthermore, in the stacking arrangement, the lower edges 292 of the lateral portions 238, 240 of the stacking aids 234, 236 of the third harvesting device 100′′ abut against the upper edges 294 of the lateral portions 238, 240 of the stacking aids 234, 236 of the second harvesting device 100′. In the stacking arrangement, the lower edges 292 of the lateral portions 238, 240 of the stacking aids 234, 236 of the fourth harvesting device 100′′′ abut against the upper edges 294 of the lateral portions 238, 240 of the stacking aids 234, 236 of the third harvesting device 100′′. Thus, the harvesting devices may rest stably on each other in the stacking arrangement.

Each of the five embodiments of a harvesting device 100, 100a, 100b, 100c, 100d described in FIGS. 1 to 7 can be considered for a system for harvesting a content of a bioreactor bag 102, comprising a bioreactor bag 102 having fixing portions 112, 114 comprising thickened portions 116, 118 at both longitudinal ends thereof and a harvesting port 115 for draining the content of the bioreactor bag 102 provided between said longitudinal ends, and a harvesting device according to one of the five embodiments of a harvesting device 100, 100a, 100b, 100c, 100d as described above.

Furthermore, the five embodiments of a harvesting device 100, 100a, 100b, 100c, 100d described in FIGS. 1 to 7 can be used for the following method for harvesting a content of a bioreactor bag 102, wherein the bioreactor bag 102 has fixing portions 112, 114 at both longitudinal ends thereof and a harvesting port 115 for draining the content of the bioreactor bag 102 provided between said longitudinal ends. The method comprises the steps of: fixing one of the fixing portions 112, 114 to the harvesting device 100, 100a, 100b, 100c, 100d by a first fixing device 104, fixing the other of the fixing portions 112, 114 to the harvesting device 100, 100a, 100b, 100c, 100d by a second fixing device 106, coupling the first fixing device 104 and/or the second fixing device 104 to the base 108 by an adjusting device 110, selectively allowing a changing of an arrangement of the first fixing portion 112 and/or the second fixing portion 114 relative to the base 108 or fixing the arrangement of the first fixing portion 112 and/or the second fixing portion 114 relative to the base 108 by the adjusting device 110, and arranging and fixing the bioreactor bag 102 in a harvesting arrangement so that the bioreactor bag 102 hangs between the first fixing device 104 and the second fixing device 106 with the harvesting port 115 being positioned substantially at the lowermost point of the bioreactor bag 102.

Thus, by the inventive harvesting device 100, 100a, 100b, 100c, 100d, the position and the arrangement of the fixing devices 104, 106 can be easily and precisely changed so that the harvesting port 115 has a position being substantially at the lowermost point of the bioreactor bag 102. This lowermost point of the bioreactor bag 102 is preferred, since harvesting, draining or transfer of the content of the bioreactor bag 102 is enabled by means of gravity. Due to the gravitational force, the content of the bioreactor bag 102 consequently leaves the bioreactor bag 102 in an advantageous manner. In this way, the content of the bioreactor bag 102 is harvested in a simplified manner, wherein at the same time a residual volume remaining in the bioreactor bag 102 after the harvesting process is reduced so that the entrapped dead volume remaining in the bioreactor bag 102 after the harvesting process is minimized.

REFERENCE LIST 100, 100a, 100b, 100c, 100d harvesting device
100′, 100a′, 100b′, 100c′, 100d′ another harvesting device
100, 100′, 100′′, 100′′′ first, second, third, and fourth harvesting devices
102 bioreactor bag
104 first fixing device
106 second fixing device
108 base
110 adjusting device
112 first fixing portion
114 second fixing portion
115 harvesting port
116 first thickened portion
118 second thickened portion
120 first clamp
122 second clamp
124 first space
126 second space
128 open end of the clamps
130 closed end of the clamps
132 upper surface of the base
134 lower surface of the base
136 stand
138, 140 support members
141 longitudinal axis of the base
142 first holding arm
144 second holding arm 146, 148 first ends of the holding arms
150, 152 second ends of the holding arms
154 first rod element of first holding arm
156 second rod element of first holding arm
158 first rod element of second holding arm
160 second rod element of second holding arm
162 first lock
164 second lock
166 first bolt
168 second bolt
170, 172 first and second attachment device
174, 176 rod elements of the attachment devices
178, 180 third and fourth locks
182, 184 bolts
186 connecting structure
188 first free end of connecting structure
190 second free end of connecting structure
192, 194 first and second uprising portion
195 bridging portion
198 attaching mechanism
202, 204 two parallel protrusions
206 attachment base
208 bolt
210 tilt axis
212 lock
214 pivoting mechanism
216 substantially planar portion
218 first end portion
220, 222 pivoting means
224 pivot axis
226 second end portion
230 first projecting element
232 second projecting element
234, 236 stacking aid
238 first lateral portion
240 second lateral portion
242 stacking aid longitudinal axis
244 first protrusion of the first lateral portion
246 second protrusion of the second lateral portion
252 first mounting recess
254 second mounting recess
256 first mounting portion
258 second mounting portion
260, 262 opposing open ends of the stacking aids
264 lateral edge of the first and second lateral portions
266 first, open end of the mounting recesses
268 second, closed end of the mounting recesses
270 mounting recess longitudinal axis
272, 274 opposing rounded edges
276 lateral edge opposing to the lateral edge 264
278 first protrusion longitudinal axis
280 second protrusion longitudinal axis
282 first connecting sheet
284 second connecting sheet
286 opening
288, 290 first and second folding axis
292 lower lateral edges of the lateral portions
294 upper lateral edges of the lateral portions

The invention claimed is:

1. A harvesting device for harvesting a content of a bioreactor bag, the bioreactor bag having fixing portions at both longitudinal ends thereof and a harvesting port for draining the content of the bioreactor bag provided between said longitudinal ends, wherein the harvesting device comprises:
a first fixing device for fixing one of the fixing portions to the harvesting device,
a second fixing device for fixing the other of the fixing portions to the harvesting device,
a base, and
an adjusting device coupling the first fixing device and/or the second fixing device to the base,
wherein the adjusting device is configured to selectively allow changing an arrangement of the first fixing portion and/or the second fixing portion relative to the base or fixing the arrangement of the first fixing portion and/or the second fixing portion relative to the base,
wherein the harvesting device is configured such that the bioreactor bag can be arranged and fixed in a harvesting arrangement in which the bioreactor bag hangs between the first fixing device and the second fixing device with the harvesting port being positioned substantially at the lowermost point of the bioreactor bag;
wherein the adjusting device comprises two holding arms,
wherein one end of each of the two holding arms is connected to the base and another end of each of the two holding arms is connected to the first fixing device and the second fixing device, respectively, and
wherein each of the two holding arms are configured such that the length thereof can be adjusted.

2. The harvesting device of claim 1, wherein the harvesting device is free of any moving device for moving the bioreactor bag and/or any tempering device for tempering the bioreactor bag, and/or
wherein the first fixing device and/or the second fixing device comprises a clamp configured to clamp the fixing portions substantially along the width thereof.

3. The harvesting device of claim 1, wherein the base comprises a stand for placing the harvesting device on a substantially horizontal surface.

4. The harvesting device of claim 1, wherein the base comprises an attaching mechanism to attach the harvesting device to a frame structure, and/or
wherein the adjusting device comprises a tilting mechanism for tilting the first fixing device and/or the second fixing device with respect to the base, wherein the tilting mechanism comprises only one rotary degree of freedom.

5. The harvesting device of claim 1, wherein the first and second fixing devices are connected to each other by a connecting structure,
wherein the connecting structure is connected to the adjusting device,
wherein the connecting structure has a substantially concave shape in cross section, and
wherein the concave shape opens upward in the harvesting arrangement.

6. The harvesting device of claim 5 wherein the connecting structure comprises a pivoting mechanism allowing the first and second fixing devices to be pivotable between the harvesting arrangement and a fixing arrangement for fixing the bioreactor bag to the harvesting device, independently from the adjusting device.

7. The harvesting device of claim 1, wherein the harvesting device further comprises a stacking aid,
wherein the stacking aid is configured to be detachably mounted to a mounting portion of the harvesting device such that another harvesting device can be arranged and stacked in a stacking arrangement with the harvesting device,
wherein the stacking aid is configured to prevent a lateral displacement of the harvesting devices relative to each other in the stacking arrangement.

8. The harvesting device of claim 7, wherein the stacking aid comprises a first lateral portion and a second lateral portion, wherein the first and second lateral portions are arranged on opposing lateral sides of a stacking aid longitudinal axis,
wherein at least one of the first and second lateral portions comprises a mounting recess configured to at least partly receive the mounting portion of the harvesting device, so as to fix the stacking aid to the harvesting device in the longitudinal direction and the lateral direction.

9. The harvesting device of claim 8, wherein the first lateral portion comprises a first protrusion and the second lateral portion comprises a second protrusion,
wherein the first and second protrusions protrude substantially in a direction perpendicular to the stacking aid longitudinal axis,
wherein the first and second protrusions extend substantially parallel to each other, and
wherein the first and second protrusions are configured to hold a holding portion of the harvesting device in the stacking arrangement.

10. The harvesting device of claim 7, further comprising two stacking aids.

11. The harvesting device of claim 1, further comprising:
the bioreactor bag having fixing portions at both longitudinal ends thereof and a harvesting port for draining the content of the bioreactor bag provided between said longitudinal ends.

12. The harvesting device of claim 11, wherein each of the fixing portions comprises a thickened portion.

13. A harvesting device for harvesting a content of a bioreactor bag, the bioreactor bag having fixing portions at both longitudinal ends thereof and a harvesting port for draining the content of the bioreactor bag provided between said longitudinal ends, wherein the harvesting device comprises:
a first fixing device for fixing one of the fixing portions to the harvesting device,
a second fixing device for fixing the other of the fixing portions to the harvesting device,
a base, and
an adjusting device coupling the first fixing device and/or the second fixing device to the base,
wherein the adjusting device is configured to selectively allow changing an arrangement of the first fixing portion and/or the second fixing portion relative to the base or fixing the arrangement of the first fixing portion and/or the second fixing portion relative to the base,
wherein the harvesting device is configured such that the bioreactor bag can be arranged and fixed in a harvesting arrangement in which the bioreactor bag hangs between the first fixing device and the second fixing device with the harvesting port being positioned substantially at the lowermost point of the bioreactor bag;
wherein the adjusting device comprises a tilting mechanism for tilting the first fixing device and/or the second fixing device with respect to the base, and
wherein the tilting mechanism comprises only one rotary degree of freedom.

14. A harvesting device for harvesting a content of a bioreactor bag, the bioreactor bag having fixing portions at both longitudinal ends thereof and a harvesting port for draining the content of the bioreactor bag provided between said longitudinal ends, wherein the harvesting device comprises:
a first fixing device for fixing one of the fixing portions to the harvesting device,
a second fixing device for fixing the other of the fixing portions to the harvesting device,
a base, and
an adjusting device coupling the first fixing device and/or the second fixing device to the base,
wherein the adjusting device is configured to selectively allow changing an arrangement of the first fixing portion and/or the second fixing portion relative to the base or fixing the arrangement of the first fixing portion and/or the second fixing portion relative to the base,
wherein the harvesting device is configured such that the bioreactor bag can be arranged and fixed in a harvesting arrangement in which the bioreactor bag hangs between the first fixing device and the second fixing device with the harvesting port being positioned substantially at the lowermost point of the bioreactor bag;
wherein the first and second fixing devices are connected to each other by a connecting structure,
wherein the connecting structure is connected to the adjusting device,
wherein the connecting structure comprises a pivoting mechanism allowing the first and second fixing devices to be pivotable between the harvesting arrangement and a fixing arrangement for fixing the bioreactor bag to the harvesting device, independently from the adjusting device.

* * * * *